United States Patent
Miyajima et al.

(10) Patent No.: US 7,455,962 B1
(45) Date of Patent: Nov. 25, 2008

(54) METHOD FOR PREPARING CELL FRACTION CONTAINING HEMANGIOBLASTS

(75) Inventors: Atsushi Miyajima, Tokyo (JP); Takahiko Hara, Chiba (JP)

(73) Assignee: Toudai TLO. Ltd., Tokyo (JP)

( * ) Notice: Subject to any disclaimer, the term of this patent is extended or adjusted under 35 U.S.C. 154(b) by 989 days.

(21) Appl. No.: 10/130,076

(22) PCT Filed: Nov. 7, 2000

(86) PCT No.: PCT/JP00/07817
§ 371 (c)(1), (2), (4) Date: Oct. 7, 2002

(87) PCT Pub. No.: WO01/34797
PCT Pub. Date: May 17, 2001

(30) Foreign Application Priority Data
Nov. 10, 1999 (JP) ................................ 11-320234

(51) Int. Cl.
*A01N 1/02* (2006.01)
*C12N 15/85* (2006.01)
(52) U.S. Cl. .......................................... 435/2; 435/325
(58) Field of Classification Search .................. 435/325
See application file for complete search history.

(56) References Cited

OTHER PUBLICATIONS

Hara et al. Identification of podocalyxin-like protein 1 as a novel cell surface marker for hemangioblasts in the murine aorta-gonad-mesenephros region. Immunity (Nov. 1, 1999) vol. 11, pp. 567-578.*
Hamaguchi et al. In vitro hematopoietic and endothelial cell development form cells expressing TEK receptor in murine aorta-gonad-mesenephros region. Blood (1999) vol. 93(5), pp. 1549-1556.*
McNagny et al. Thrombomuciin, a novel cell surface protein that defines thrombocytes and multipoteitic progenitors. The Journal of Cell Biology (1997) vol. 138 (6), pp. 1395-1407.*

(Continued)

*Primary Examiner*—Celine X Qian
(74) *Attorney, Agent, or Firm*—Wilmer Cutler Pickering Hale & Dorr LLP

(57) ABSTRACT

Mouse PCLP1 was identified by expression cloning with the use of a monoclonal antibody against a surface antigen of a cell line derived from mouse AGM. By fractionating PCLP1-positive/CD45-negative cells and culturing them in vitro, it was clarified that these cells differentiate into endothelial-like cells, angioblast-like cells, and hematopoietic cells. By transferring the PCLP1-positive/CD45-negative cells into a mouse defective in the hematopoietic function, the hematopoietic system was reconstructed over a long period of time. These facts indicate that the PCLP1-positive/CD45-negative cells contain mammalian hemangioblasts capable of expressing the activity as long-term repopulating hematopoietic stem cells (LTR-HSC). The present invention provides a method for preparing a cell fraction containing hemangioblasts, the cell fraction prepared by the method, and use of this cell fraction.

4 Claims, 21 Drawing Sheets

OTHER PUBLICATIONS

Doyannas et al. Podacalyxin is a CD34-related marker of murine hematopoieic stem cells and embryonic erythroid cells. Blood (2005) vol. 105(11), pp. 4170-4178.*

Nishikawa et al. Preogressive lineage analysis by cell sorting and culture identifies FLK1+VE-cadhedrin cells at a dvierging point of endothelial and hematopoietic lineages. Development (1998) vol. 125, pp. 1747-1757.*

Kershaw et al., 1997, JBC, vol. 272, No. 25, pp. 15708-15714.*

Onitsuka et al. Blood, 2005, vol. 106, No. 11, part1, pp. 641A.*

Nishikawa et al., "In Vitro Generation of Lymphohematopoietic Cells from Endothelial Cells Purified from Murine Embryos," Immunity, vol. 8, Jun. 1998, pp. 761-769.

Asahara et al., (1997) Science, 275, pp. 964-967.

Bjornson et al., (1999) Science 283, pp. 534-537.

Choi et al., (1998) Development 125, pp. 725-732.

Cumano et al., (1996) Cell 86, pp. 907-916.

Delassus and Cumano, (1996) Immunity 4, pp. 97-106.

Dickson et al., (1995) Development 121, pp. 1845-1854.

Dzierzak et al., (1998) Immunol. Today, 19, pp. 228-236.

Eichmann et al., (1997) Proc. Natl. Acad. Sci. USA 94, pp. 5141-5146.

Gerig et al., (1998) EMBO J. 17, pp. 4029-4045.

Godin et al., (1995) Proc. Natl. Acad. Sci. USA 92, pp. 773-777.

Goldstein et al., (1979) Proc. Natl. Acad. Sci. USA 76, pp. 333-337.

Gonzalez, et al. (1991) Agricultura Revista Agropecuaria 60, pp. 804-805.

Hamaguchi et al., (1999) Blood 93, pp. 1549-1556.

Hara et al., (1998) Dev. Biol. 201, pp. 144-153.

Hara et al., (Nov. 1999) Immunity, 11, pp. 567-578.

Harada et al., (1990) Proc. Natl. Acad. Sci. USA 87, pp. 857-861.

Hirashima et al., (1999) Blood 93, pp. 1253-1263.

Hockfield et al., (1993) "Selected Methods for Antibody and Nucleic Acid Probes", vol. 1 (New York: Cold Spring Harbor Laboratory Press).

Ichihara, et al., (1997) Blood 90, pp. 165-173.

Imakawa et al., (1995) Endocrine 3, pp. 511-517.

Jaffredo et al., (1998) Development 125, pp. 4575-4583.

Keller et al., (1999) Exp. Hematol. 27, pp. 777-787.

Kershaw et al., (1995) J. Biol. Chem. 270, pp. 29439-29446.

Kershaw et al., (1997) J. Biol. Chem 272, pp. 15708-15714.

Kodama et al., (1994) Exp. Hematol. 22, pp. 979-984.

Liao et al., (1998) Genes Dev. 12, pp. 621-626.

McNagny et al., (1997) J. Cell Biol. 138, pp. 1395-1407.

Monopoli, et al., (1991) Informatore Agrario 47, pp. 23-26.

Morrison et al., (1995) Annu. Rev. Cell. Dev. Biol. 11, pp. 35-71.

Motsenbocker, et al., (1994) Louisiana Agric. Exper. Station Mimeo Series 88, pp. 14-15.

Mouse rat, Accession No. AB020726.

Mukouyama et al., (1998) Immunity 8, pp. 105-114.

Muller et al. (1994) Immunity, 1, pp. 291-301.

Murray, (1932) Proc. Roy. Soc. London 11, pp. 497-521.

Nishikawa et al., (1998) Development 125, pp. 1747-1757.

Nishikawa et al., (1998) Immunity 8, pp. 761-769.

Ogorochi et al., (1992) Blood 79, pp. 895-903.

Okabe et al., (1997) FEBS Lett. 407, pp. 313-319.

Pardanaud et al., (1996) Development 122, pp. 1363-1371.

Pardanaud et al., (1999) Development 126, pp. 617-627.

Picha, et al., (1994) Louisiana Agric. Exper. Station Mimeo Series 88, pp. 16-17.

Pitchaimuthu, et al., (2001) South Indian Hort. 49, pp. 311-312.

Porcher et al., (1996) Cell 86, pp. 47-57.

Sabin, (1920) Contributions to Embryology 9, pp. 213-262.

Sanchez et al., (1996) Immunity 5, pp. 513-525.

Sassetti et al., (1998) J. Exp. Med. 187, pp. 1965-1975.

Schuh et al., (1999) Proc. Natl. Acad. Sci. USA 96, pp. 2159-2164.

Shalaby et al., (1995) Nature 376, pp. 62-66.

Shalaby et al., (1997) Cell 89, pp. 981-990.

Takahashi et al., (1999) Nat. Med. 5, pp. 434-438.

Tanaka et al., (1999) Blood 93, pp. 804-815.

Tavian et al., (1996) Blood 87, pp. 67-72.

Tavian et al., (1999) Development 126, pp. 793-803.

Visvader et al., (1998) Genes Dev. 12, pp. 473-479.

Voyta et al., (1984) J. Cell Biol. 99, pp. 2034-2040.

Wagner, (1980) Adv. Microcirc. 9, pp. 45-75.

Yoder et al., (1996) Biol. Blood Marrow Transplant. 2, pp. 59-67.

Yoder et al., (1997) Immunity 7, pp. 335-344.

* cited by examiner

Fluorescent intensity

Figure 3

```
mouse PCLP1      1:MPPTTALSALLLLLLSPASHSH-NGNETSTSAIKSST-VQSHQSATTSTEVTTGHPVAST  58
human PCLP1      1:MRCALALSAL-LLLLSTPP-LL-PSSPSPSPSP-SPSQ-NA-TQTTTD-SSNKTAPTPAS  53
rabbit PCLP1     1:MRSALALAALLLLLLSPPSLSQEKSPQPGPTPMATSTSTRPAPASAPAPKSSVAASVPAE  60
Thrombomucin     1:MRAPLLLPLLPLLLPGVSSGNNDKTTHSTTVSPETTKQITTITVTTSQVQGSISASKPSS  60 mouse PCLP1     59:LAST-QPSNPTP-FT-TSTQSPFMPTSTPNP-TSNQSGGNLTSSVSEVDKTKTSSPSSTA 114
human PCLP1     54:SV-T-IMATDTAQQSTVPTSKANEILASV--KATTL--GVSSDSP-GTTTLAQQVS-GP- 104
rabbit PCLP1    61:QNTT-PMTTKAP-ATQSPSASPGSSVENSAP-AQGSTTTQQSLSVTTKAEAKDAGGVPTA 117
Thrombomucin    61:TAPT-AVMSPTKAQEAATSSKQHDSSTSSIPPPSTSITPSIITTSPQGKTPSTPALTHTPD 120 mouse PCLP1    115:FTSSSGQTASSGGK-SG-DSFTT-APTT-TL-G-----L---INVSSQ---PTDLNTTSKL 159
human PCLP1    105:VNT-TVARGGGSGN-P-TTTIESPK-STK-SAD--TTTVA-TSTAT-AK-PNTTSSQ--- 151
rabbit PCLP1   118:HVTGSARPVTSGSQVAAQDPAASKAPSNHSITTKP---LA-TEATSQ--APRQTTDVGTP 171
Thrombomucin   121:QNTKTTGRQDDTSHVSVASTSASQQVSSSASAAVPTTTSAVTSSATQQKVSPTDSSEILL 180 mouse PCLP1    160:LST--PTTDNTTSPQQPVDSSPSTASHP--VG-QHTPAAV-PSSSGSTPSTDNSTLTWKP 213
human PCLP1    152:N-GAE-DTTN-SG-GKSSHS-VTTDLTSTK-AEHLTTP-HP-TSPLSPRQ-P--T-L--T 197
rabbit PCLP1   172:GPTA-PPVTNSTSPDLLGHATPKPSEGP-QLSFPTAAGSLGPVTGSGTGSGTLSTPQGKP 229
Thrombomucin   181:KPSASPNSTQVTSPSRTPKGFLSTVTTSPHIADNGSTALNQLKSTVSSSEVPVSSFLDKD 240 mouse PCLP1    214:TTHKPLGTSEATQ-----PL--TSQTP-GITTLPVS-TLQQSM-ASTVGTT-TEEFT-H- 260
human PCLP1    198:HPVATPTSSGHDHLMKISSSSSTVAIPGYTFTSP--G-MTTTLPSSVISQRTQQTSSQMP 254
rabbit PCLP1   230:ATLTPVASSAETQGM-PSPMPPSPASP-SSSPFPSPSPSPALQPSGPSAAGTEDTTGRG 287
Thrombomucin   241:HSVSSSTSATNQHL-SLSSHRPTSPVPKFECSTPHSGSVPSTSSKTSLSSPSSSTKNATV 299 mouse PCLP1    261:LISNGTPVAP-P--GPSTPSPIWAFGNYQLNCEP-PIRPDEELL-ILN--LTR--ASLC- 310
human PCLP1    255:ASSTAPSSQETVQPTSPATALRTPTLPETMSSSP-TAASTTHRYPKTPSPTVAHESNWAKC 314
rabbit PCLP1   288:PTSSSTELASTALHGPSTLSPTSAVRDQRVSCGP-PERPTEQLL-ILN--LTR--SSPCI 341
Thrombomucin   300:TTTMTTAKAAYTSQGDGSVTHKSGVTAQSPTSAPLPTPTLKDHMKSKSPDQTHSNVSPPN 359 mouse PCLP1    311:---ER-S---------PLD--EK---E-KLVELLCHSVKASFKPAEDLCTLHVAPI 347
human PCLP1    315:EDLETQTQSEKQLVLNLTGNTLCAG--GASDEKLISLICRAVKATFNPAQDKCGIRLASV 372
rabbit PCLP1   342:HVFQRQSQGE-GET-EI---SMHSTDSL-PEDKLVTLLCRAAKPTFNPAQDQCHVLLAPM 395
Thrombomucin   360:EVICEDQIGEVRPILNLKEEKTCDDWKKASNEAFFEVFCSGRRHAFNSTRDRCFVKLAS- 418 mouse PCLP1    348:LDNQAVAVKRIIIETKLSPKAVYELLKDRWDDLTEAGVSDMKLGKEGPPEVNEDRFSLPL 407
human PCLP1    373:PGSQTVVVKEITIHTKLPAKDVYERLKDWDELKEAGVSDMKLGDQGPPEEAEDRFSMPL 432
rabbit PCLP1   396:LGSHAVVVKEITIKTNLLPTAVFELLKDRWDDLREEGVSDMQLGDQGPPEETEDRFSLPL 455
Thrombomucin   419:SNHRRWAV-HVIVHRVLPPAAVFEELKEKRNELEKLGITNVTYLNQEMEEEIKDQSSTPL 477 mouse PCLP1    408:IITIVCMASFLLLVAALYGCCHQRISQRKDQQRLTEELQTVENGYHDNPTLEVMETPSEM 467
human PCLP1    433:IITIVCMASFLLLVAALYGCCHQRLSQRKDQQRLTEELQTVENGYHDNPTLEVMETSSEM 492
rabbit PCLP1   456:IITIVCMASFLLLVAALYGCCHQRLSHRKDQQRLTEELQTVENGYHDNPTLEVMETSAEM 515
Thrombomucin   478:IITIVTLAGSLLLIAAIYGCCHQRFSQKKSQQRLTEELQTMENGYHDNPTLEVMETGSEM 537 mouse PCLP1    468:QEKKVVNLNGELGDSWIVPLDNLTKDDLDEEDTHL 503 (SEQ ID NO: 2)
human PCLP1    493:QEKKVVSLNGELGDSWIVPLDNLTKDDLDEEDTHL 528 (SEQ ID NO: 3)
rabbit PCLP1   516:QEKKVVNLNGELGDSWIVPLDNLTKDDLDEEDTHL 551 (SEQ ID NO: 4)
Thrombomucin   538:QEKK-VNLNGELGDSWIVPLDTIMKEDL-EEDTHL 571 (SEQ ID NO: 5)
```

METHOD FOR PREPARING CELL FRACTION CONTAINING HEMANGIOBLASTS

CROSS-REFERENCE TO RELATED APPLICATIONS

This application is a 371 of PCT/JP00/07817 filed Nov. 7, 2000, which claims the benefit of Japanese patent application Ser. No. 11/320,234 filed Nov. 10, 1999. The contents of these applications are incorporated by reference in their entirety.

TECHNICAL FIELD

The present invention relates to a marker molecule for hemangioblasts, method for preparing a cell fraction containing hemangioblasts using the marker molecule, cell fraction prepared by the method, and use of the cell fraction.

BACKGROUND ART

Development of hematopoiesis proceeds through two distinct steps, i.e. primitive and definitive hematopoiesis. In mice, primitive hematopoiesis begins in the extraembryonic yolk sac at 7.5 days post coitum (dpc) in gestation, while definitive hematopoiesis, which is distinguished by enucleated erythrocytes, lymphopoiesis, and generation of long term repopulating hematopoietic stem cells (LTR-HSCs), originates from the intraembryonic aorta-gonad-mesonephros (AGM) region at 10.5 to 11.5 dpc (Muller, A. M. et al. (1994) Immunity, 1, 291-301) (also reviewed by (Dzierzak, E. et al. (1998) Immunol. Today 19, 228-236; Keller, G et al. (1999) Exp. Hematol. 27, 777-787). Within 1 to 3 days of their emergence, LTR-HSCs migrate from the AGM region to the fetal liver and then emigrate to the bone marrow just before birth. Lymphopoietic cells and multi-potential hematopoietic progenitors are also detected in the para-aortic splanchnopleura (P-Sp) region of mouse embryos at 7.5 to 9.5 dpc (Cumano, A. et al. (1996) Cell 86, 907-916; Delassus, S., and Cumano, A. (1996) Immunity 4, 97-106; Godin, I. et al. (1995) Proc. Natl. Acad. Sci. USA 92, 773-777), an intraembryonic site preceding the AGM region. However, LTR-HSCs, which are capable of repopulating lethally irradiated adult mice, have not been found in the P-Sp region. Interestingly, it was recently reported that LTR-HSCs can be detected in the yolk sac and the P-Sp region after transplantation into the livers of busulfan-treated newborn mice (Yoder, M. C. et al. (1997) Immunity 7, 335-344). Therefore, one speculation has been that LTR-HSCs generated in these sites lack homing capacity to the bone marrow and that the phenotypic differences in hematopoiesis between the yolk sac, the P-Sp region, and the AGM region can be mostly attributed to the supporting microenvironment. However, it still remains unknown how LTR-HSCs in the yolk sac acquire full repopulation activity.

Early in the last century, detailed observations of the early development of chick embryos led to the hypothesis that hematopoietic cells and endothelial cells arise from a common precursor termed the hemangioblast (Murray, P. D. F. (1932) Proc. Roy. Soc. London 11, 497-521; Sabin, F. R. (1920) Contributions to Embryology 9, 213-262) [also reviewed by (Wagner, R. C. (1980) Adv. Microcirc. 9, 45-75)]. In the last 5 years, a number of studies have provided evidence supporting this hypothesis. First, a series of elegant grafting experiments using chicks and quails demonstrated that the splanchnopleural mesoderm is able to generate hematopoietic cells and endothelium, while the paraxial mesoderm lacks this hematogenic capacity (Pardanaud, L. et al. (1996) Development 122, 1363-1371). Hematogenic activity in the former region is regulated by endoderm-derived cytokines such as vascular endothelial growth factor (VEGF), basic fibroblast growth factor (bFGF), and transforming growth factor β1 (TGFβ1), whereas ectodermal factors such as epidermal growth factor (EGF) suppress it in the latter region (Pardanaud, L. and Dieterlen-Lievre, F. (1999) Development 126, 617-627). In the splanchnopleural mesoderm, cells expressing VEGF receptor 2 (VEGF-R2) were shown to form both hematopoietic and endothelial colonies (Eichmann, A. et al. (1997) Proc. Natl. Acad. Sci. USA 94, 5141-5146). Furthermore, endothelial cells in the dorsal aorta generated $CD45^+$ hematopoietic cells in vivo as evidenced by cell labeling experiments using DiI-labeled acetylated low density lipoprotein (DiI-Ac-LDL) (Jaffredo, T. et al. (1998) Development 125, 4575-4583).

While similar in vivo grafting experiments are not possible in mammalian systems, it was found that hematopoietic cells were clustered at the ventral wall of the dorsal aorta in a 5 week-old human embryo (Tavian, M. et al. (1996) Blood 87, 67-72). More recently, Tavian et al. showed that $CD34^+$ cells in the dorsal aorta and vitelline artery of human embryos are capable of generating hematopoietic cells in vitro (Tavian, M. et al. (1999) Development 126, 793-803). In mice, Nishikawa et al. recently showed that cells expressing Flk1 (mouse counterpart of VEGF-R2) and vascular endothelial cadherin (VECadherin) in the yolk sac and the P-Sp region of mouse embryos at 9.5 dpc gave rise to lymphohematopoietic cells in vitro (Nishikawa, S. et al. (1998) Immunity 8, 761-769). Similarly, $Flk1^+$ hematogenic endothelial cells were generated from ES cells in vitro (Choi, K. et al. (1998) Development 125, 725-732; Nishikawa, S. I. et al. (1998) Development 125, 1747-1757). The idea that putative hemangioblasts express Flk1 arose originally from the finding that knockout mice lacking Flk1 exhibited severe defects in both hematopoiesis and vasculogenesis in the yolk sac (Shalaby, F. et al. (1995) Nature 376, 62-66). Furthermore, Flk1-null cells did not contribute to definitive hematopoiesis (Shalaby, F. et al. (1997) Cell 89, 981-990), although a recent report suggested that a significant number of hematopoietic cells can be induced from Flk1-null ES cells in vitro (Schuh, A. C. et al. (1999) Proc. Natl. Acad. Sci. USA 96, 2159-2164).

In conformity with the critical role of TGFβ1 in the induction of hematopoiesis and vasculogenesis in chick embryos, knockout mice deficient in TGFβ1 also exhibited severe defects in both systems (Dickson, M. C. et al. (1995) Development 121, 1845-1854). Furthermore, gene disruption of the SCL/Tal-1 transcription factor caused defects in both hematopoiesis and vasculogenesis which were similar to those of Flk1 knockout mice (Porcher, C. et al. (1996) Cell 86, 47-57: Visvader, J. E. et al. (1998) Genes Dev. 12, 473-479). Mutant zebrafish devoid of the SCL/Tal-1 gene also showed similar defects (Liao, E. C. et al. (1998) Genes Dev. 12, 621-626) and forced expression of SCL/Tal-1 in zebrafish embryos resulted in the overproduction of hematopoietic and vascular cells (Gering, M. et al. (1998) EMBO J. 17, 4029-4045). Taken together, these studies clearly demonstrate the presence of hemangioblasts, the common precursors of both hematopoietic and endothelial cells, in fish, avian, and mammalian embryos and that VEGF-R2/Flk1, TGFβ1, and SCL/Tal-1 are essential for the development of hemangioblasts. However, the nature of hemangioblasts remains unexplored, in particular, there is yet no absolute evidence that LTR-HSCs are derived from hemangioblasts.

DISCLOSURE OF THE INVENTION

An objective of the present invention is to provide a novel marker molecule for hemangioblasts, method for preparing a cell fraction containing hemangioblasts using the marker molecule, cell fraction prepared by the method, and use of the cell fraction.

The Inventors characterized the nature of mammalian hemangioblasts by using their AGM primary culture system, in which multipotential hematopoietic progenitor cells and endothelial-like cells expand in vitro (Mukouyama, Y. et al. (1998) Immunity 8, 105-114). In this culture, oncostatin M (OSM), a member of the IL-6 family of cytokines, is essential for the expansion of both cell types. Although OSM plays an essential role in the expansion of both cell populations, OSM does not directly stimulate the growth of hematopoietic progenitors in colony forming assays (data not shown). The inventors thus hypothesized that endothelial-like cells may contain hemangioblasts that produce hematopoietic progenitors in the AGM culture.

In order to isolate a novel marker molecule of endothelial-like cells in AGM culture, the present inventors prepared a monoclonal antibody against endothelial-like cells and conducted expression cloning using the antibody. As a result, the inventors succeeded in cloning a gene encoding the mouse counterpart (mouse PCLP1) corresponding to human and rabbit podocalyxin-like protein 1 (PCLP1).

Furthermore, the present inventors investigated properties of PCLP1+CD45 cells in the AGM region to find out the formation of both hematopoietic cells and endothelial cells from PCLP1+CD45− cells in vitro. By injecting PCLP1+CD45− cells into neonatal livers of busulfan-administered mice, the inventors further demonstrated that a plurality of hematopoietic cell lineages are produced over a long period of time in vivo, thereby proving for the first time that mammalian hemangioblasts are capable of constructing LTR-HSCs.

More specifically, PCLP1+CD45 cells thus selected exhibited endothelial-like morphology, incorporated acetylated low-density lipoprotein, and proliferated in response to OSM. In the co-presence of OP9 stromal cells together with VEGF and OSM, almost all the PCLP1+CD45− cells became positive for CD34, CD31 and VECadherin (FIG. 15), acquiring a capability to form a cellular network in the matrigel substrate (FIG. 16). These results indicate that PCLP1+CD45− cells have angioblast activity, and that OSM is essential for their proliferation and differentiation. On the other hand, DiI+CD45− endothelial-like cells (cf. examples) in the AGM primary culture generated hematopoietic cells in vitro (FIG. 1), and PCLP1+CD45− cells selected above similarly generated hematopoietic cells in vitro in the presence of hematopoietic growth factors and OP9 cells (FIG. 17). Most important finding was that PCLP1+CD45− cells reconstructed the entire hematopoietic system over a long period of time when transplanted into busulfan-treated neonatal mice (FIGS. 18 to 21, and Table 1).

Thus, the present invention identifies PCLP1 as a novel cell marker for discriminating a cell fraction containing hemangioblasts and provides a method for preparing a cell fraction containing hemangioblasts using this marker.

As described above, although Nishikawa et al. previously reported the possibility that Flk1 and VECadherin could be marker molecules for hemangioblasts (Nishikawa, S. I. et al. (1998) Development 125, 1747-1757; Nishikawa, S. I. et al. (1998) Immunity 8, 761-769), expression level of PCLP1 is extremely high compared to those of Flk1 and VECadherin, which makes PCLP1 an excellent marker for first separating hemangioblasts.

More specifically, the present invention comprises:

(1) a method for preparing a cell fraction containing hemangioblasts, wherein said method comprises separating cells comprising a PCLP1-positive phenotype, (2) the method according to (1), which further comprises separating cells comprising a CD45-negative phenotype, (3) the method according to (1) or (2), wherein said cells are separated from cells derived from the aorta-gonad-mesonephros (AGM) region, (4) a PCLP1-positive cell fraction containing hemangioblasts that is prepared by a method according to any one of (1) through (3), (5) the cell fraction according to (4), which generates or contains long-term repopulating hematopoietic stem cells (LTR-HSCs).

(6) a cell composition containing the cell fraction according to (4) and a culture medium, (7) a method for preparing a chimeric animal, wherein said method comprises transplanting the cell fraction according to (4), (8) a chimeric animal transplanted with the cell fraction according to (4), (9) the chimeric animal according to (8), wherein donor (transplanted cells)-derived blood cells can be reconstructed,

(10) the chimeric animal according to (8) or (9), wherein said animal is mouse,

(11) a DNA according to any one of the following (a) through (c), wherein the DNA encodes the mouse-derived PCLP1 protein:

(a) a DNA comprising the coding region of the nucleotide sequence set forth in SEQ ID NO: 1, (b) a DNA encoding a protein comprising the amino acid sequence set forth in SEQ ID NO: 2, and (c) a DNA encoding a protein comprising the amino acid sequence set forth in SEQ ID NO: 2 in which one or more amino acids are substituted, deleted, inserted, and/or added,

(12) a protein encoded by the DNA according to (11),

(13) a vector into which the DNA according to (11) has been inserted,

(14) a host cell carrying the vector according to (13),

(15) a method for preparing the protein according to (12), wherein said method comprises the steps of culturing the host cell according to (14) and collecting expressed proteins from said host cell or culture supernatant thereof,

(16) an antibody against PCLP1 protein, wherein the antibody is used for detecting or separating a cell fraction containing hemangioblasts,

(17) the antibody according to (16) that binds to a protein as defined in (12),

(18) a separation reagent for a cell fraction containing hemangioblasts, wherein said reagent comprises the antibody according to (16) or (17),

(19) an antibody that specifically binds to mouse-derived PCLP1 protein,

(20) an antibody that binds to a peptide comprising the amino acid residues at positions 1 to 405 in the amino acid sequence set forth in SEQ ID NO: 2,

(21) a peptide containing a partial sequence comprising at least 7 or more consecutive amino acid residues at positions 1 to 405 in the amino acid sequence set forth in SEQ ID NO: 2, and,

(22) a polynucleotide comprising at least 15 nucleotides, wherein the polynucleotide is complementary to DNA comprising the nucleotide sequence set forth in SEQ ID NO: 1 or to the complementary strand thereof, and is used in the amplification and detection of the expression of the DNA according to (11), or in the expression control of the DNA.

Besides mouse PCLP1, "PCLP1s" of the present invention includes, unless the origin is otherwise specified, PCLP1s derived from vertebrates including human or rabbit podocalyxin-like protein 1 (PCLP1) (Kershaw, D. B. et al. (1997) J. Biol. Chem. 272, 15708-15714; Kershaw, D. B. et al. (1995) J. Biol. Chem. 270, 29439-29446), preferably PCLP1s derived from mammals. Similarly, "CD45s" of the present invention includes CD45s derived from vertebrates, preferably CD45s derived from mammals.

Herein, "hemangioblasts" refers to cells capable of generating both endothelial cells and hematopoietic cells.

"Endothelial cells" refers to adherent cells showing endothelial cell morphology, namely polygonal morphology when cultured in vitro, which have the activity to incorporate acetylated low density lipoprotein. In this invention, more preferably, endothelial cells can proliferate in response to a stimulation by OSM. Even more preferably, in endothelial cell differentiation culture systems, cells positive for hematopoietic cell markers such as CD34, CD31, and VECadherin could be generated when co-cultured with OP9 stromal cells in the presence of VEGF, OSM, etc. Also, still more preferably, endothelial cells can give rise to a cellular network formation in matrigel plate assays. These properties can be assayed according to methods described in Examples.

"Hematopoietic cells" refers to cells expressing a hematopoietic cell phenotype, meaning spherical non-adherent cells with a CD45- or Ter119-positive phenotype. During their differentiation, hematopoietic cells specifically express combinations of B220, Mac-1, Gr-1, Thy-1, CD4, CD8, etc. as lineage markers.

"Hematopoietic cells" includes "hematopoietic stem cells". These hematopoietic stem cells are preferably CD45-positive. Preferably, when co-cultured with OP9 cells in the presence of hematopoietic growth factors including SCF, interleukin (IL)-3, erythropoietin (EPO), etc., hematopoietic stem cells generate myeloid (e.g. Mac-1/Gr-1-positive), lymphoid (e.g. B220/Thy-1-positive) or erythroid (e.g. Ter119-positive) cells. Alternatively, hematopoietic stem cell phenotype can be confirmed by reconstruction of hematopoietic stem cells or blood cells derived from transplanted cells that are transplanted into animals lacking hematopoietic functions.

In this invention, "long term repopulating hematopoietic stem cells (LTR-HSCs)" refers to hematopoietic stem cells capable of reconstructing hematopoiesis over a long duration.

The present invention provides a method for preparing a cell fraction containing hemangioblasts, characterized by separating cells expressing a PCLP1 (podocalyxin-like protein 1)-positive (described as PCLP$^+$) phenotype.

As cells used in the aforementioned separation, tissues and cells presumed to contain hemangioblasts, or hemangioblast cultures, may be used. Most preferable cells are those derived from the aorta-gonad-mesonephros (AGM) region. These cells may be vertebrate-derived, preferably mammalian cells (for example, cells from rodents), or may be human cells. In mice, cells derived from the intraembryonic AGM region at 10 to 11.5 dpc, which corresponds to the AGM region of a 4 to 5 week-old human embryo, are preferable in particular.

Moreover, since it has been suggested that dorsal aorta-associated endothelial cells contain the budding site of hematopoietic cells (Tavian, M. et al. (1996) Blood 87, 67-72; Tavian, M. et al. (1999) Development 126, 793-803), hemangioblasts are highly likely to exist in this region. Furthermore, the present inventors indicate the possibility of the presence of hemangioblasts in the genital ridge region (F, I, O in FIGS. 10 to 11). Therefore, cells derived from these regions can be also used.

OSM-dependant proliferation of hematopoietic precursor cells and endothelial-like cells were also observed in a primary culture of the P-Sp region of an embryo at 9.5 dpc similarly to a culture of AGM derived from a mouse embryo at 11.5 dpc. Although such a proliferation was not observed in the yolk sac at 9.5 dpc, PLCP1$^+$CD45$^-$ cells were present in both yolk sac and P-Sp region (data not shown). Therefore, cells derived from the yolk sac and P-Sp region are highly likely to contain hemangioblasts. Therefore, cells such as these can also be used in the separation in this invention.

It is also possible to isolate PLCP1$^+$ cells or PLCP1$^+$CD45$^-$ cells using ES-derived cells. Generation and proliferation of LTR-HSC from ES cells are also important in the application of human ES cells. Furthermore, recently, CD34$^+$ blood progenitor endothelial cells were found in peripheral blood, which were shown to be bone marrow-derived (Asahara, T. et al. (1997) Science 275, 964-967; Takahashi, T. et al. (1999) Nat. Med. 5, 434-438). Very recently, Bjornson et al. reported that LTR-HSCs are derived from cultured neural stem cells in vivo (Bjornson, C. R. et al. (1999) Science 283, 534-537). Therefore, it is likely that hemangioblasts exist in these tissues besides embryonic hematopoietic sites. In this invention, such cells may also be also used for isolating PLCP1$^+$ cells or PLCP1$^+$CD45$^-$ cells.

Neonatal and adult tissues, for example, umbilical cord and bone marrow can be also used. Separation of hemangioblasts using the method of this invention is extremely significant in the clinical application of these cells.

Separation of PLCP1$^+$ cells can be performed, for example, by cell sorting as described in Examples using anti-PCLP1 antibody.

In this invention, in order to obtain cell fractions containing hemangioblasts in a high concentration, it is preferable to separate cells further expressing the CD45 phenotype in addition to the PLCP1$^+$ phenotype. Separation of cells having the PLCP1$^+$CD45$^-$ phenotype can be performed, for example, according to methods described in Examples. PLCP1$^+$ cell fraction or PLCP1$^+$CD45$^-$ cell fraction containing hemangioblasts can be further subdivided using different cell markers.

For example, in the present invention, it may be useful to fractionate CD34$^+$ cells from PCLP1$^+$ cell fraction or PLCP1$^+$CD45$^-$ cell fraction. In Examples, the inventors have identified PCLP1 as a marker for hemangioblasts. PCLP1 is a highly glycosylated protein with some similarity to CD34, a conventional marker for LTR-HSCs. Interestingly, both PCLP1 and CD34 are ligands for L-selectin in the lymphocyte-high endothelium venule and contain conserved amino acid sequences in their cytoplasmic regions (Sassetti, C. et al. (1998) J. Exp. Med. 187, 1965-1975), suggesting an overlapping function between the two molecules. In fact, both PCLP1 and CD34 are expressed in the dorsal aortic endothelium and the genital ridge region (FIGS. 10 and 11) and as much as 91% of CD34$^+$ cells in the AGM region also express PCLP1 (FIG. 8, right). In chicken, thrombomucin, an avian counterpart of PCLP1, is expressed in hematopoietic progenitors and thrombocytes (McNagny, K. M. et al. (1997) J. Cell Biol. 138, 1395-1407), however no avian CD34 has been identified. Therefore, the functions, if any, of CD34 might be compensated by PCLP1. Sanchez et al. showed that LTR-HSCs in the AGM region are CD34$^+$c-Kit$^+$ (Sanchez, M. J. et al. (1996) Immunity 5, 513-525) and LTR-HSCs in the yolk sac and P-Sp region were also found in the CD34$^+$c-Kit$^+$ fraction (Yoder, M. C. et al. (1997) Immunity 7, 335-344).

Since PCLP1$^+$CD34$^+$CD45$^-$ cells (12% of the PCLP1$^+$ CD45$^-$ cells) exist in the AGM region (FIG. 8, right), the LTR-HSC activity found in the CD34$^+$ fraction might represent, in part, that of the hemangioblasts. Thus, the PCLP1$^+$ CD34$^+$CD45$^-$ cells in the AGM region are important as a cellular fraction containing hemangioblasts, and are likely to contain a high concentration of LTR-HSCs that are capable of reconstructing, in particular, hematopoietic systems.

Furthermore, in this invention, it may be also useful to fractionate Flk1-positive cells from the PCLP1$^+$ cell fraction or the PLCP1$^+$CD45$^-$ cell fraction. Recently, Nishikawa et al. demonstrated the hematopoietic activity in an Flk1$^+$VECadherin$^+$CD45$^-$ cell population derived from the yolk sac and P-Sp region of mouse embryo at 9.5 dpc (Nishikawa, S. I. et al. (1990) Immunity 8, 761-769). Studies on ES differentiation in vitro and Flk1-knockout mice also indicated that putative hemangioblasts express Flk1 (Choi, K. et al. (1998) Development 125, 725-732; Nishikawa, S. I. et al. (1998) Development 125, 1747-1757; Shalaby, F. et al. (1995) Nature 376, 62-66). In accordance with these results, one fraction (12%) of PLCP1$^+$CD45$^-$ cells in the AGM region expressed Flk1 (FIG. 9, left), and PLCP1$^+$CD45$^-$ cells cultured in the presence of OSM were all Flk1-positive (FIG. 14, below). In contrast, frequency of VECadherin$^+$ cells in the PLCP1$^+$CD45$^-$ cell population in the AGM region was very low (3%) (FIG. 9, right). From these findings, PLCP1$^+$CD45$^-$ Flk1$^+$ cells in AGM region are important as a cell fraction containing hemangioblasts.

Cell fractions prepared in the present invention can be cultured or stored in an appropriate medium, which may be supplemented with serum, growth/differentiation factors, etc. As a medium, for example, DMEM containing 15% FCS supplemented with OSM and SCF, or the like can be used.

Among cells contained in cell fractions of this invention, long-term repopulating hematopoietic stem cells (LTR-HSCs) are important in particular. Presence of LTR-HSC in a cell fraction can be confirmed by transplanting the cell fraction into an animal made deficient in hematopoietic functions to prepare a chimeric animal, and assaying the capability of the cells to reconstruct the hematopoietic system.

As described in Examples, chimeric animals can be prepared by transplanting the cell fraction of this invention into livers of neonatal mice in which the hematopoietic function has been destructed by busulfan administration.

There is no restriction on the type of animals used for preparing chimeras, examples being mice, rabbits, other large-sized animals, etc.

Establishment of chimerism can be confirmed by examining the post-transplantational generation of donor-derived blood cells.

In chimeric animals transplanted with the cell fraction of this invention containing LTR-HSCs, donor (transplanted cells)-derived LTR-HSC is generated in the recipient reconstructing the hematopoietic system. Inclusion of LTR-HSC in transplanted cells can be confirmed by the appearance of donor-derived lymphoid, myeloid, and erythroid cells above the detection limit (for example, 1% or more) in recipients. In addition, occurrence of a long-term reconstruction of hematopoiesis can be confirmed by detecting donor-derived blood cells at least 60 days, more preferably 180 days after the transplantation of LTR-HSC.

PLCP1$^+$CD45$^-$ cells and recipients transferred with the cells are useful in the screening of drugs that control the proliferation and differentiation of hemangioblasts. For example, by adding a test compound to PLCP1$^+$CD45$^-$ cells in culture, effects of the compound on the proliferation, differentiation, hematopoietic function, and the like of the cells can be examined. By administering a test compound to a recipient (for example, mouse) transplanted with PLCP1$^+$ CD45$^-$ cells, effects of the compound on hematopoiesis of the recipient can be also investigated.

Furthermore, the present invention relates to an antibody against the PCLP1 protein used for the detection or separation of cell fractions containing hemangioblasts. This invention also relates to the use of an antibody raised against the PCLP1 protein in the detection or separation of cell fractions containing hemangioblasts. Such an antibody binds to the cell surface PCLP1 protein. Such an antibody is suitably prepared by using the extracellular domain of the PCLP1 protein as an antigen, or cells expressing the PCLP1 protein as an immunogen as described in Examples.

There is no particular restriction on the animal species from which the PCLP1 protein that is used as the immunogen is derived, and it maybe human (J. Biol. Chem. 272: 15708-15714 (1997)), mouse, rat (Accession number: ABO20726), rabbit (J. Biol. Chem. 270: 29439-29446 (1995)), chicken (J. Cell Biol. 138: 1395-1407 (1997)), or another vertebrate. Antibodies can be prepared according to methods well-known in the field. For example, in the case of a monoclonal antibody, it may be prepared by the rat foot-pad immunization method (Hockfield, S. et al. (1993) "Selected Methods for Antibody and Nucleic Acid Probes", Volume 1 (New York: Cold Spring Harbor Laboratory Press)), etc.

Such an antibody can be appropriately combined with buffers and stabilizers to make a reagent for detecting or separating cell fractions containing hemangioblasts. This antibody may also become a test reagent for cell fractions containing hemangioblasts. The antibody may be fluorescence-labeled.

The present invention also provides the mouse PCLP1 protein. The mouse PCLP1 gene was isolated by expression cloning using a monoclonal antibody against the cell surface antigen on a mouse AGM region-derived cell line (LO cells). The nucleotide sequence of cDNA encoding the mouse PCLP1 protein isolated by the present inventors is set forth in SEQ ID NO: 1, and the amino acid sequence of the mouse PCLP1 protein encoded by the cDNA is set forth in SEQ ID NO: 2, respectively. PLCP1$^+$ cell fractions contain hemangioblasts capable of generating endothelial cells and hematopoietic cells.

Proteins of this invention include, as long as they can serve as marker molecules for hemangioblasts (for example, proteins with overlapping antigenicities), not only the wild type PCLP1 protein (SEQ ID NO: 2), but also proteins structurally analogous thereto. Such structurally analogous proteins include mutants of the wild type mouse PCLP1 protein. Whether antigenicity is overlapped or not can be determined by immunizing a recipient animal with the wild type mouse PCLP1 protein as antigen and examining whether the antibody thus produced has a reactivity toward a protein of interest. Alternatively, the above test can be performed by preparing an antibody against a protein of interest to determine the reactivity of the protein with the wild type mouse PCLP1 protein.

Such proteins include not only naturally occurring mutants but also artificially prepared mutants that can be produced by those skilled in the art, for example, using the known method for mutagenesis. Methods known to those skilled in the art for modifying amino acids in proteins are exemplified by Kunkel's method and PCR.

In artificial alteration of amino acids in proteins, the number of amino acid residues to be altered is usually 30 or less, preferably 10 or less, and more preferably 5 or less. An amino acid having properties similar to those of the amino acid to be substituted is preferably used for substitution. For example, since Ala, Val, Leu, Ile, Pro, Met, Phe, and Trp are all classified into the non-polar amino acid group, they are considered to have similar properties. Non-charged amino acids include Gly, Ser, Thr, Cys, Tyr, Asn, and Gln. Acidic amino acids include Asp and Glu, while basic amino acids include Lys, Arg, and His.

The protein of this invention can be prepared as either a natural protein or a recombinant protein utilizing gene recombination techniques. Natural proteins can be prepared by, for example, subjecting extracts from tissues and cells that are presumed to express mouse PCLP1 protein (for example, LO cells, embryo cells in AGM region, etc.) to affinity chromatography using the above-described antibody to the mouse PCLP1 protein. On the other hand, recombinant proteins may be prepared by culturing cells transformed with DNA encoding the mouse PCLP1 protein, allowing the transformants to express the protein, and recovering the protein as described below. Proteins of this invention can be fused to peptide tags and other proteins. Such fusion proteins can be useful for facilitating the purification and detection of proteins.

The present invention also includes partial peptides of the protein of this invention. Partial peptides of this invention include peptides containing partial sequences comprising at least 7 or more consecutive amino acid residues, preferably 8 amino acid residues or more, and more preferably 9 amino acid residues or more in the region specific (at positions 1 to 405 of the amino acid sequence set forth in SEQ ID NO: 2) to mouse PCLP1. An antibody specifically binding to the mouse-derived PCLP1 protein can be obtained by preparing the antibody using the above-described partial peptides as antigens. Examples of partial peptides of this invention are, for example, those of the N-terminal region of proteins of this invention (for example, SEQ ID NO: 2) and intracellular domain thereof, and these can be used in the antibody preparation. Furthermore, in the mouse PCLP1 protein (SEQ ID NO: 2), peptides containing the regions comprising 12 amino acid residues at positions 440 to 451, 10 amino acid residues at positions 464 to 473, or 4 amino acid residues at positions 500 to 503 in the intracellular domain analogous to CD34 are considered to be useful as partial peptides to search functions common to both CD34 and PCLP1. Partial peptides of this invention can be produced by, for example, genetic engineering techniques, known peptide synthesis methods, or by digestion of the protein of this invention with appropriate peptidases.

This invention also relates to DNAs encoding the proteins of the invention. DNAs encoding the protein of this invention are not particularly limited as long as they can encode the proteins of this invention, including cDNAs, genomic DNAs, and synthetic DNAs. DNAs having any desired nucleotide sequence based on the degeneracy of genetic code are also included in this invention as long as they can encode the proteins of this invention.

cDNAs encoding the proteins of this invention can be screened, for example, by labeling cDNA of SEQ ID NO: 1 or segments thereof, RNAs complementary to them, or synthetic oligonucleotides comprising partial sequences of the cDNA with $^{32}$P, etc., and hybridizing them with a cDNA library derived from tissues (e.g., cells derived from AGM region of embryo, etc.) expressing the proteins of this invention. Alternatively, such cDNAs can be cloned by synthesizing oligonucleotides corresponding to nucleotide sequences of these cDNAs, and amplifying them by PCR with cDNA derived from suitable tissues (e.g. cells derived from AGM region of embryo, etc.) as a template. genomic DNA can be screened, for example, by labeling cDNA of SEQ ID NO: 1 or segments thereof, RNAs complementary to them, or synthetic oligonucleotides comprising partial sequences of the cDNA with $^{32}$P, etc., and hybridizing them with a genomic DNA library. Alternatively, the genomic DNA can be cloned by synthesizing oligonucleotides corresponding to nucleotide sequences of these cDNAs, and amplifying them by PCR with genomic DNA as a template. Synthetic DNAs can be prepared, for example, by chemically synthesizing oligonucleotides comprising partial sequences of cDNA of SEQ ID NO: 1, annealing them to form a double strand, and ligating them with DNA ligase.

These DNAs are useful for the production of recombinant proteins. A protein of this invention can be prepared as a recombinant protein by inserting the DNA encoding the protein (e.g. DNA of SEQ ID NO: 1) into an appropriate expression vector, transforming suitable cells with the vector, culturing the transformants, and purifying the expressed protein from the transformants or their culture supernatant.

There is no limitation on the host and vector to be used, and it is possible to use a prokaryotic or eukaryotic system. Specifically, for example, COS7 cells and the pME18S vector can be used. A vector can be introduced into cells by a known method, for example, DEAE-dextran method (Blood 90: 165-173, 1997) for mammalian cells.

Recombinant proteins expressed in host cells can be purified by known methods. The protein of this invention expressed in the form of a fusion protein, for example, with a histidine residue tag or glutathione-S-transferase (GST) attached to the N-terminus can be purified by a nickel column or a glutathione sepharose column, etc.

The present invention also provides a polynucleotide containing at least 15 nucleotides complementary to the DNA comprising the nucleotide sequence of SEQ ID NO: 1 or to the complementary strand thereof, which is used to amplify a DNA encoding a mouse PCLP1 protein, detect the expression, or regulate the expression. Herein, the term "complementary strand" refers to one strand of a double strand polynucleotide comprising A:T (A:U) and G:C base pairs, when viewed against the other strand. Furthermore, "complementary" means not only when a nucleotide sequence is completely complementary to a continuous nucleotide sequence with at least 15 nucleotides, but also when there is an identity of at least 70%, preferably at least 80%, more preferably 90%, and much more preferably 95% or more at the nucleotide sequence level. The identity can be determined by BLAST. Polynucleotides include DNA and RNA. Nucleotide derivatives can also be included.

Such polynucleotides include probes, primers, nucleotides or nucleotide derivatives (e.g. antisense oligonucleotides and ribozymes, etc.), which can specifically hybridize with DNAs encoding mouse PCLP1 proteins, or DNAs complementary to said DNAs.

cDNAs encoding the proteins of this invention or oligonucleotides comprising partial sequences thereof can be used for cloning genes and cDNAs encoding the proteins of this invention, or amplifying them by PCR. They can also be used as, for example, probes for Northern blot analyses, or as primers for RT-PCR to detect or quantify the expression. The cDNAs and oligonucleotides can also be utilized for detecting polymorphism or an aberration (gene diagnosis, etc.) of the gene or cDNA by the restriction fragment length polymorphism (RFLP) method, single strand DNA conformation polymorphism (SSCP) method, etc. It is also possible to suppress the expression of the mouse PCLP1 protein using an antisense polynucleotide.

The present invention also provides an antibody specific to mouse PCLP1. The antibody may be prepared by extracting sequences specific to the mouse PCLP1 protein based on a comparison of the amino acid sequence of mouse PCLP1 protein with those of PCLP1 proteins derived from other vertebrates, and immunizing appropriate animals with peptides having said sequences as described above. There is no limitation in the region of these peptides that is used for the immunization as long as they are immunogenic. Antibodies of this invention include, for example, those binding to peptides comprising the amino acid residues at positions 1 to 405 set forth in SEQ ID NO: 2.

Antibodies thus prepared can be utilized, besides in cell sorting, for example, in the affinity purification of proteins of this invention, test and diagnosis of disorders in patients or in disease models having disorders caused by an expressional aberration, or structural abnormality of a protein of this invention, and the like, and also in the detection of the expression levels of the inventive proteins. More specifically, aberrations in the expression and structure of proteins of this invention can be tested and diagnosed by using methods such as FACS, Western blotting, immunoprecipitation, ELISA, immunohistochemical technique, etc. to detect the proteins in samples extracted from tissues, blood, cells, or tissue segments.

Prior arts and other references cited in the present specification are all incorporated herein as a part thereof.

Endothelial-like cells generated in a day 6 AGM primary culture were pulse labeled with DiI-Ac-LDL for 6 h. DiI$^+$ CD45$^-$ cells (RI fraction) were then isolated by FACS and inoculated into an unlabeled day 6 AGM culture. After a 4-day chase culture, both floating and adherent cells were analyzed by FACS. DiI$^+$CD45$^+$ hematopoietic cells (shown by "1") were generated from the DiI-labeled endothelial-like cells. CD45$^+$ cells in the adherent cell fraction are likely to be cobble stone-forming cells and cells attached to the stromal cell layer.

Figure 2A:
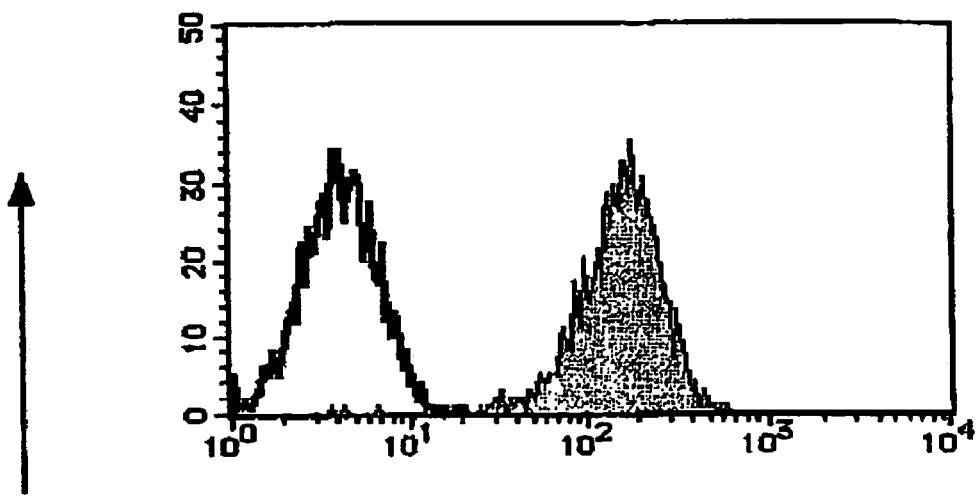
Figure 2B:
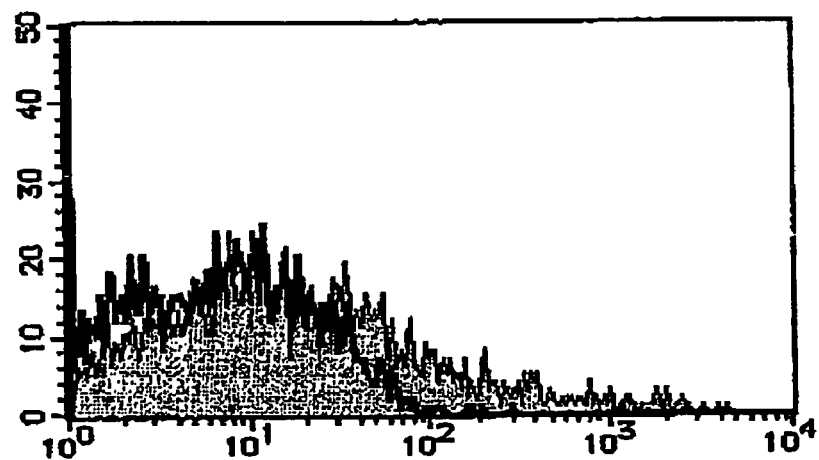

FIG. 2 is a diagram representing cloning and expression of mouse PCLP1.

(A) FACS staining of LO cells with 10B9 monoclonal antibody (shaded peak) or isotype control (blank peak).

(B) FACS staining of COS7 cells transfected with mouse PCLP1 cDNA (shaded peak) or mock vector (blank peak) with 10B9 antibody.

FIG. 3 is a diagram representing an alignment of amino acid sequences of mouse (SEQ ID NO: 2), human (SEQ ID NO: 3), and rabbit PCLP1 (SEQ ID NO: 4), and avian thrombomucin (SEQ ID NO: 5). The underline and double-underlines represent signal peptides and transmembrane domains, respectively. In human PCLP1, the reported signal peptide contains two extra amino acid residues in addition to the underlined residues ( . . . LP).

Figure 4:
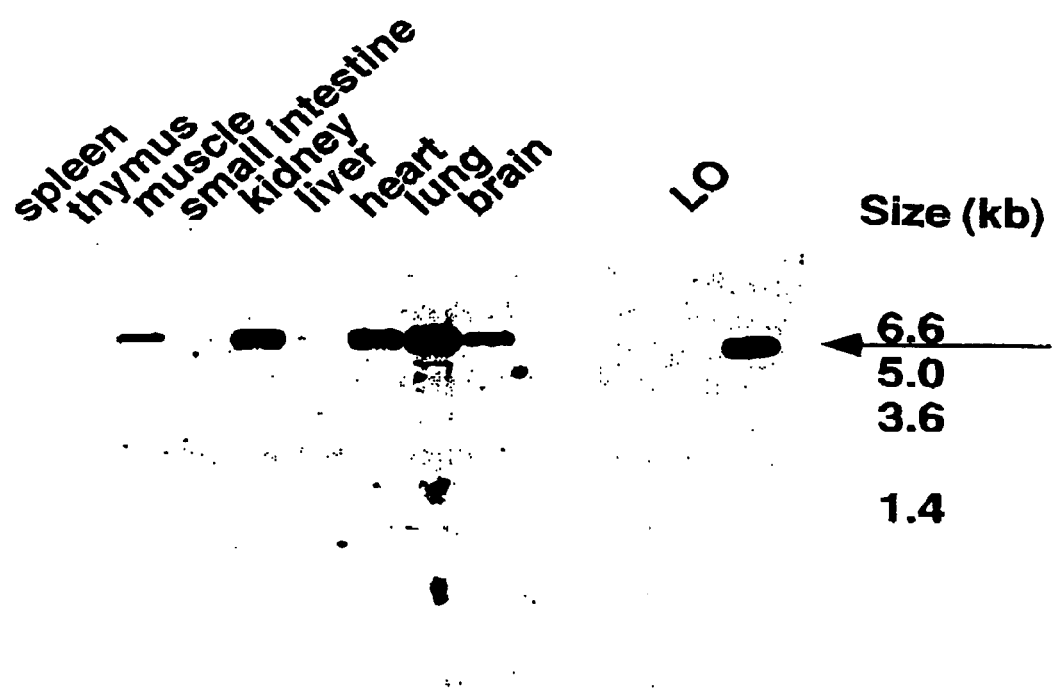

FIG. 4 is a photograph representing the result of Northern blot analysis of PCLP1 mRNA in various mouse adult tissues and LO cells. PolyA$^+$ RNA (1 µg) was loaded in each lane.

Figure 5A:
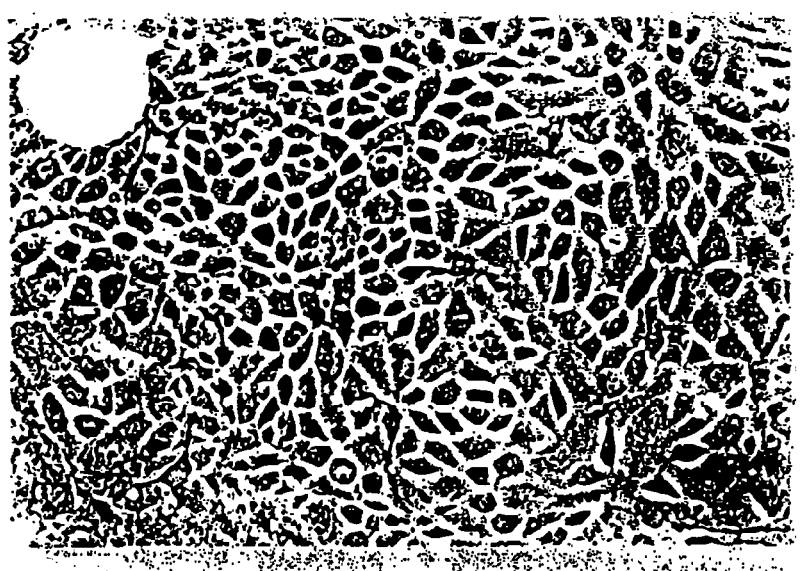
Figure 5B:
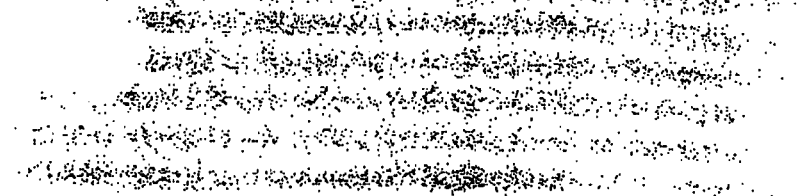
Figure 5C:

FIG. 5 is a photograph representing the expression of PCLP1 in an AGM culture.

(A) Morphological appearance of endothelial-like cells in the AGM primary culture on day 6.

(B, C) Immunostaining of endothelial-like cells in the AGM culture with isotype control (B) or 10B9 anti-PCLP1 antibody (C). Original magnification: (A) 100×; (B, C) 200×.

Figure 6:
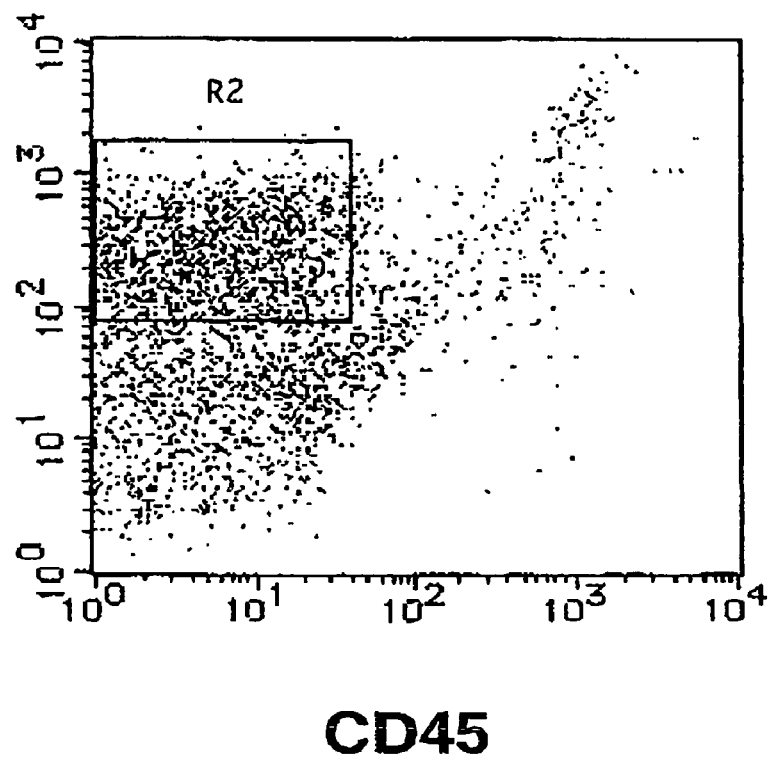

FIG. 6 is a diagram representing the expression of PCLP1 and CD45 in an AGM culture. Represents a FACS analysis of the total cells in the AGM culture on day 6 with anti-PCLP1 and anti-CD45 antibodies. R2 gated cells were sorted as a PCLP1$^+$CD45$^-$ fraction for the co-culture experiment shown in FIG. 7.

Figure 7:
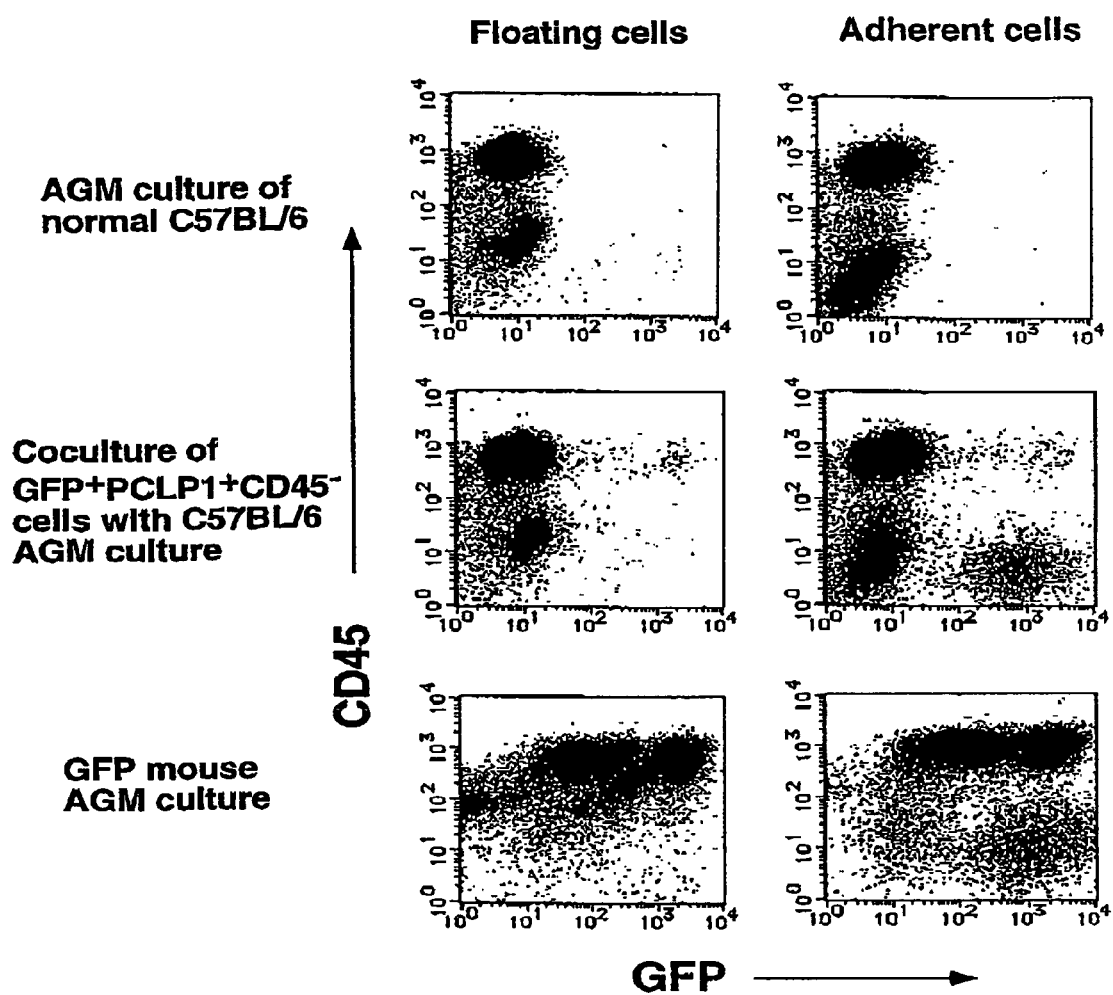

FIG. 7 is a diagram representing the result of the FACS analysis of the floating cells and adherent cells in a co-culture (middle panel) where the PCLP1$^+$CD45$^-$ cells from the AGM culture of GFP mice were sorted on day 6 and co-cultured with the AGM culture of normal mice for 4 more days. Upper and bottom panels are negative (AGM culture of normal mice) and positive (AGM culture of GFP mice) controls for the detection of GFP, respectively. Note that GFP$^+$CD45$^+$ cells are generated from PCLP1$^+$CD45$^-$ cells in the co-culture.

FIG. 8 is a diagram representing the result of FACS analyses of the AGM region of mouse embryos.

(A) Expression of PCLP1 and CD45 in cells from the AGM region. A single cell suspension prepared from the AGM regions of mouse embryos at 11.5 dpc was stained with anti-CD45 antibody and anti-PCLP1 antibody or isotype control and analyzed by FACS.

(B) Expression of CD31 and CD34 in the CD45$^-$ cell population. The AGM-derived cells were stained with anti-PCLP1 antibody and anti-CD45 antibody together with either anti-CD34 or anti-CD31 antibodies. FACS profiles of PCLP1 and CD34 or CD31 in the CD45$^-$ cell fraction are shown. Note that most of CD34$^+$ and CD31$^+$ cells are included in the PCLP1$^+$CD45$^-$ cell fraction.

Figure 9A:
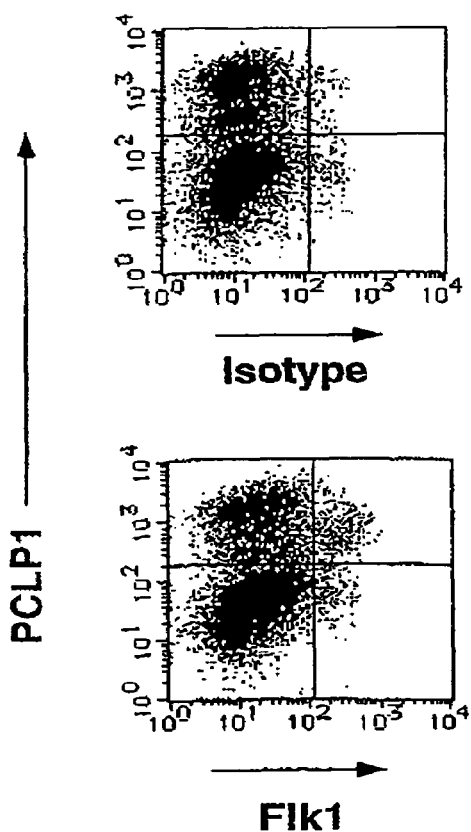
Figure 9B:
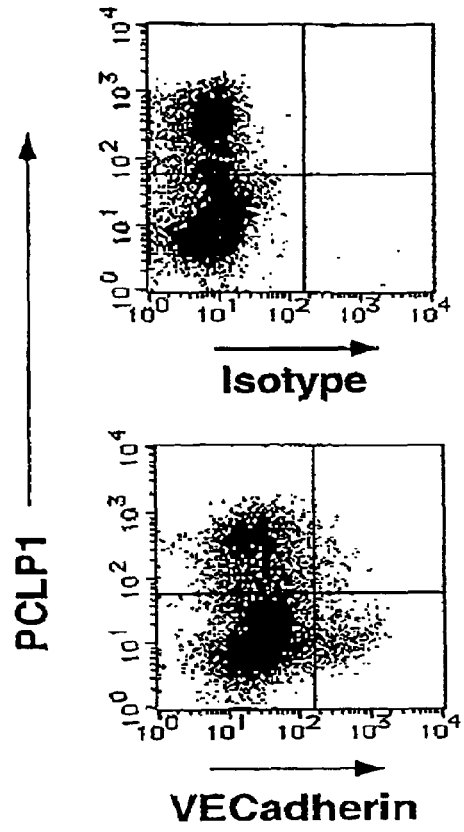

FIG. 9 is a diagram representing the result of FACS analysis of the AGM region of mouse embryos.

Shows the expression of Flk1 and VECadherin in the CD45$^-$ cell population. The AGM-derived cells were stained with anti-PCLP1 and anti-CD45 antibodies together with either anti-Flk1 antibody (C) or anti-VECadherin antibody (D). Expression patterns of PCLP1 and Flk1 (C) or VECadherin (D) in the CD45$^-$ cell fraction are presented.

Figure 10:
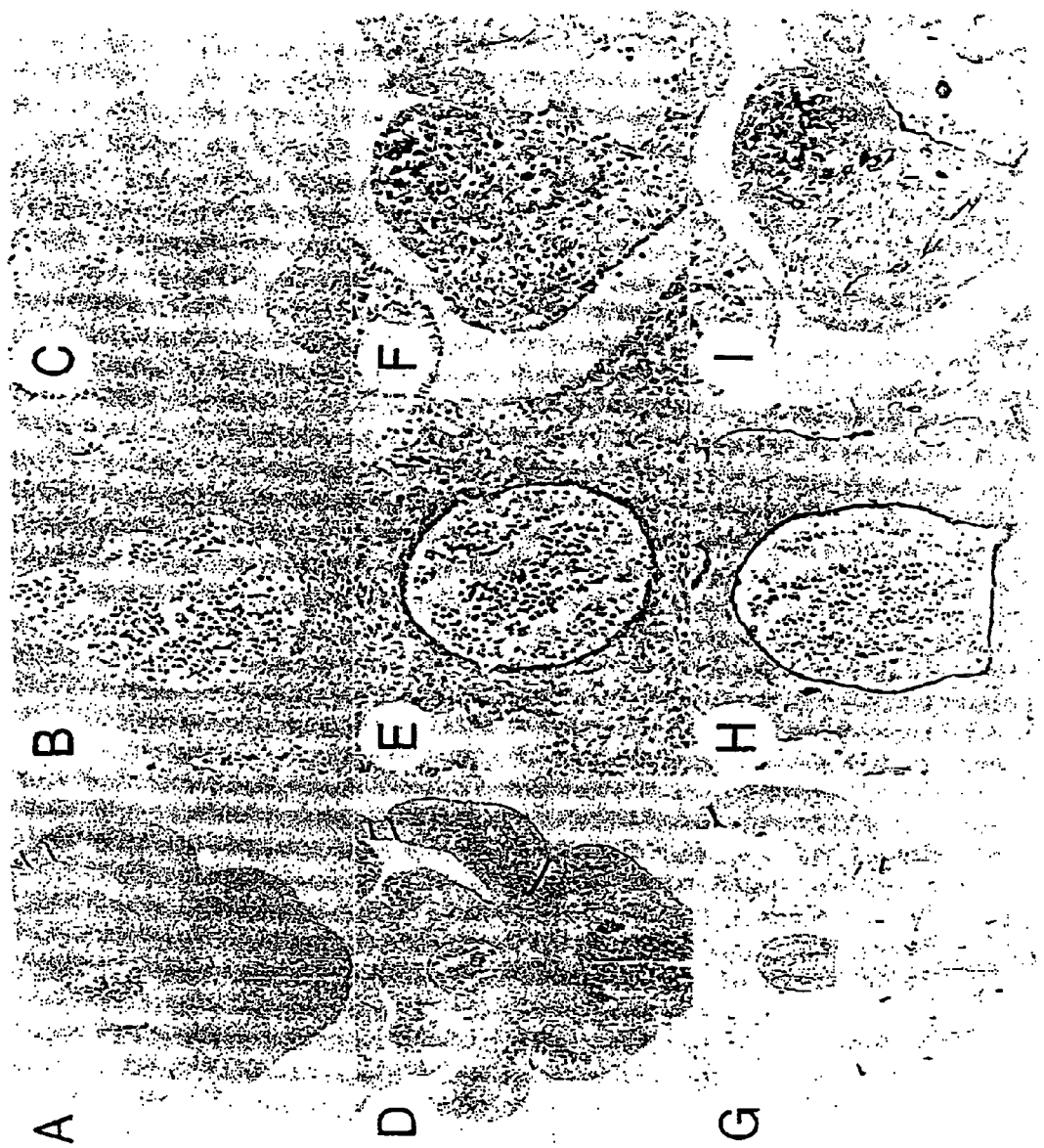

FIG. 10 is a photograph representing an expression of PCLP1 in the AGM region of a mouse embryo.

(A to I) Paraffin sections of the AGM region of a mouse embryo at 11.5 dpc were stained immunohistochemically with isotype control (A to C), anti-PCLP1 (D to F), or anti-CD34 (G to I) antibodies. Expression of PCLP1 and CD34, shown in brown, mostly overlap in the aorta (E, H) and genital ridge regions (F, I).

Figure 11:
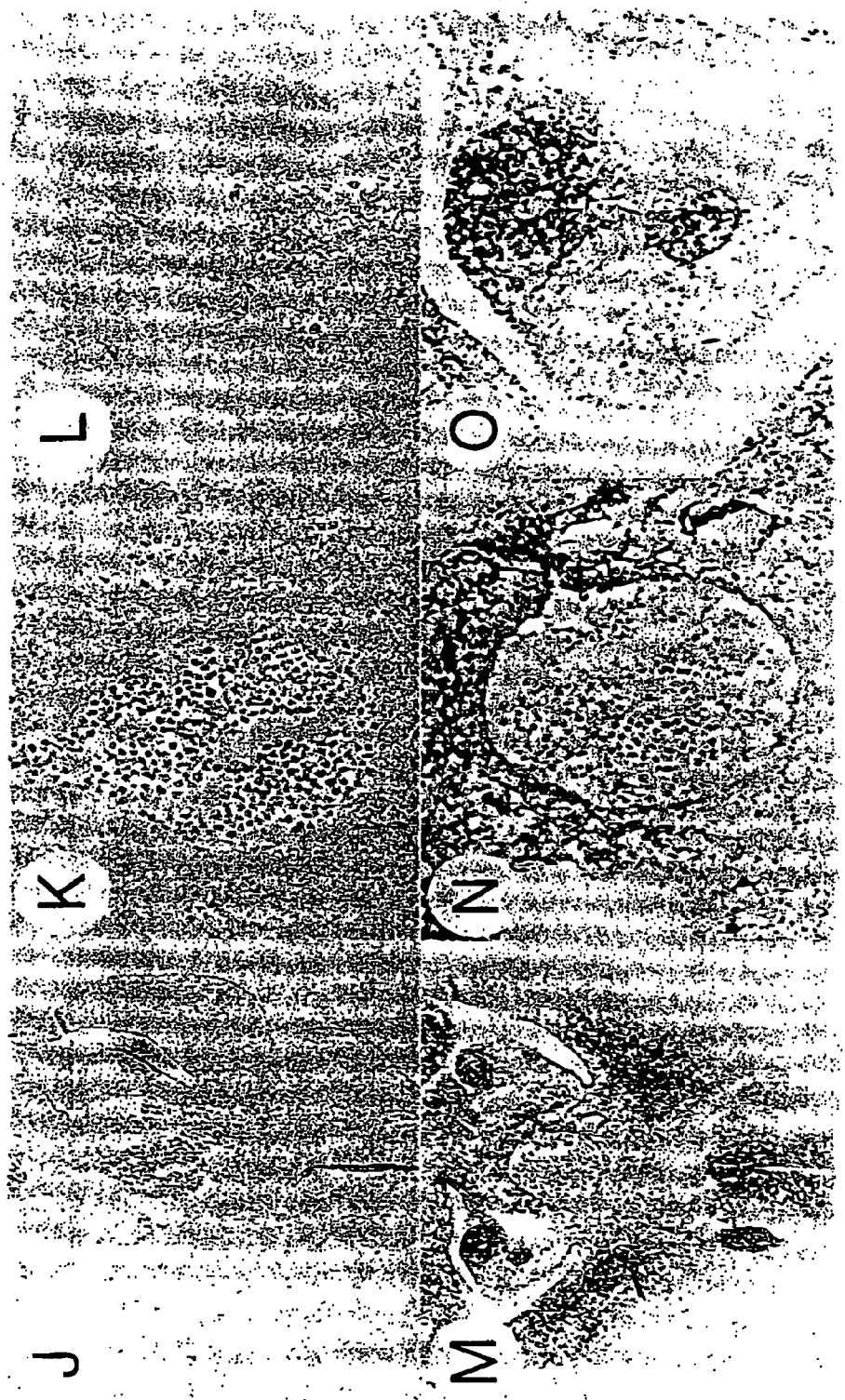

FIG. 11 is a photograph representing an expression of PCLP1 in the AGM region of a mouse embryo.

(J to O) Paraffin sections of the AGM region were subjected to in situ hybridization using sense (J to L) or anti-sense (M to O) cRNA to the mouse PCLP1 cDNA as a probe. Specific signals are shown in dark blue. Original magnification was 40× (left panels). Aorta and genital ridge regions are further enlarged in middle and right panels, respectively.

Figure 12:
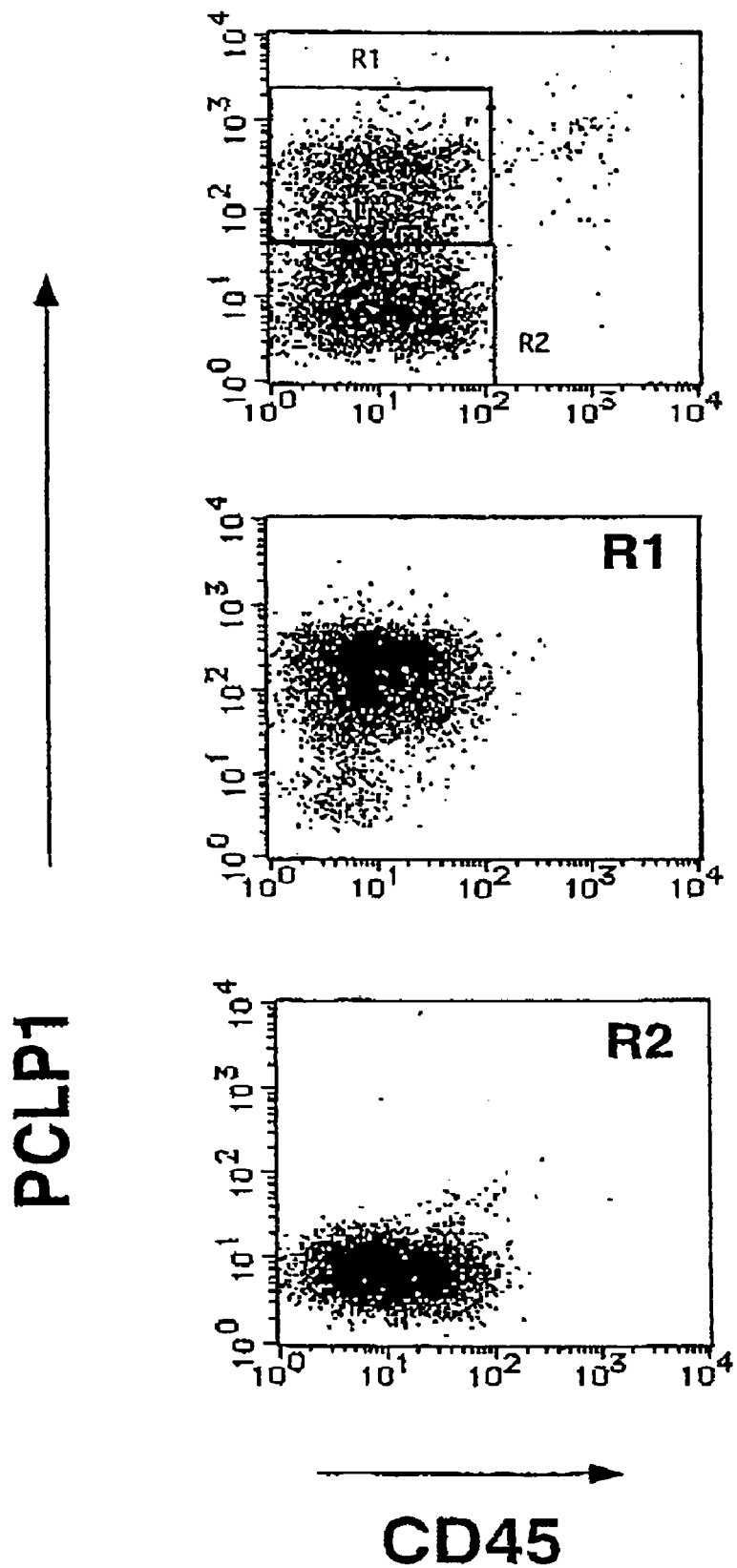

FIG. 12 is a diagram representing differentiation of PCLP1$^+$CD45$^-$ cells into endothelial cells.

Shows the FACS analysis of the cells in the AGM regions of mouse embryos at 11.5 dpc with anti-PCLP1 and anti-CD45 antibodies. In lower panels, sorted PCLP1$^+$CD45$^-$ cells (R1 gate) or PCLP1$^-$CD45$^-$ cells (R2 gate) were reanalyzed, respectively.

Figure 13:
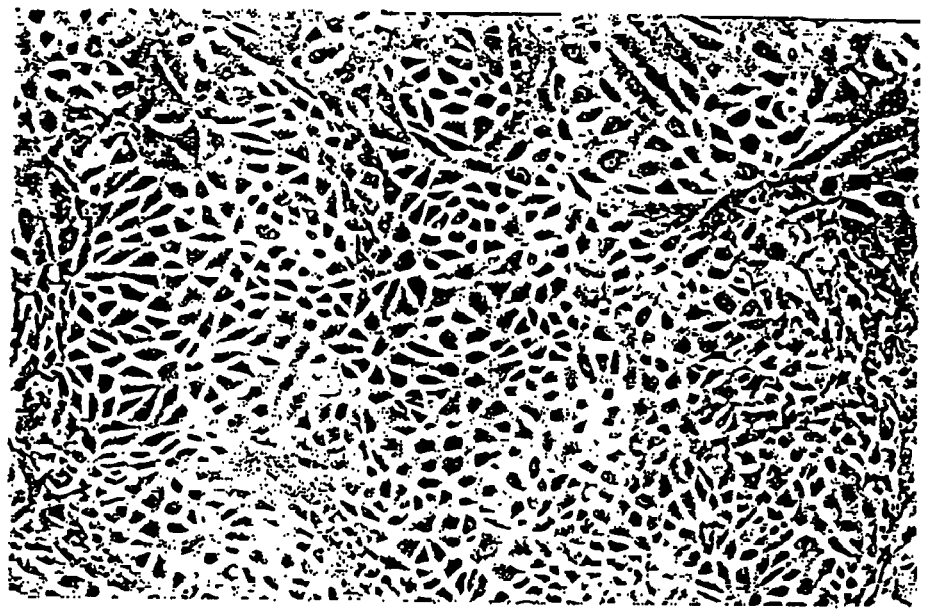

FIG. 13 is a photograph representing differentiation of PCLP1$^+$CD45$^-$ cells into endothelial cells.

Morphological appearance of the sorted PCLP1$^+$CD45$^-$ cells from the AGM region after 6 days in culture with SCF and OSM.

Figure 14A:
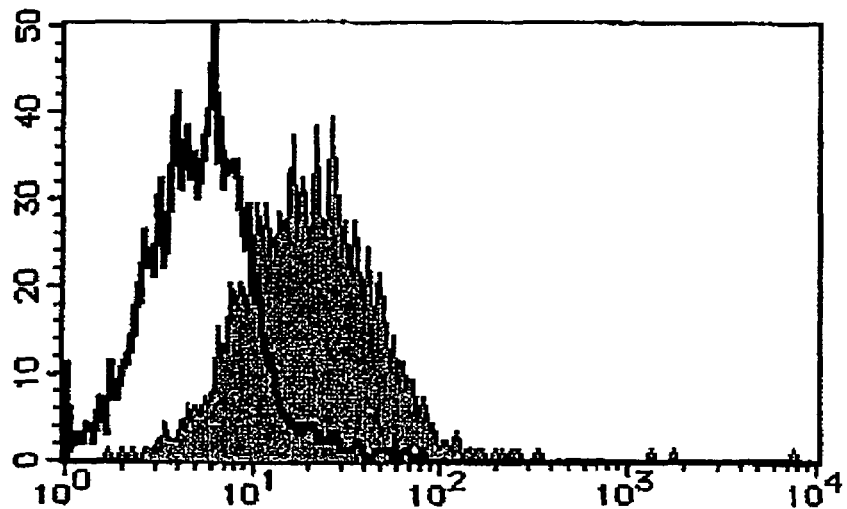
Figure 14B:
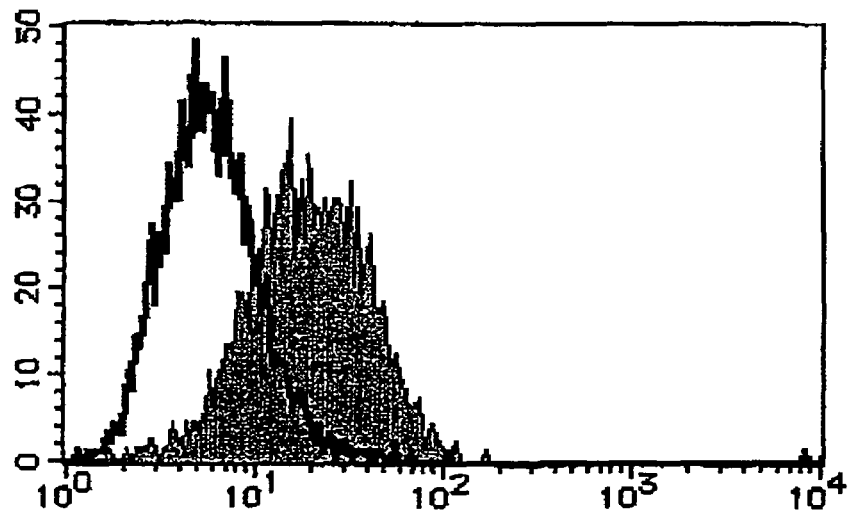

FIG. 14 is a diagram representing differentiation of PCLP1⁺CD45⁻ cells into endothelial cells.

Top panel: Incorporation of DiI-labled acetylated LDL into PCLP1⁺CD45⁻ cells after 6 days in culture. Shaded and blank peaks represent FACS patterns of cells incubated with or without DiI-acetylated LDL, respectively.

Bottom panel: Expression of Flk1 on the PCLP1⁺CD45⁻ cells after 6 days in culture. Cells were stained with anti-Flk1 (shaded peak) or isotype control (blank peak) antibody and subjected to FACS analysis.

Figure 15:
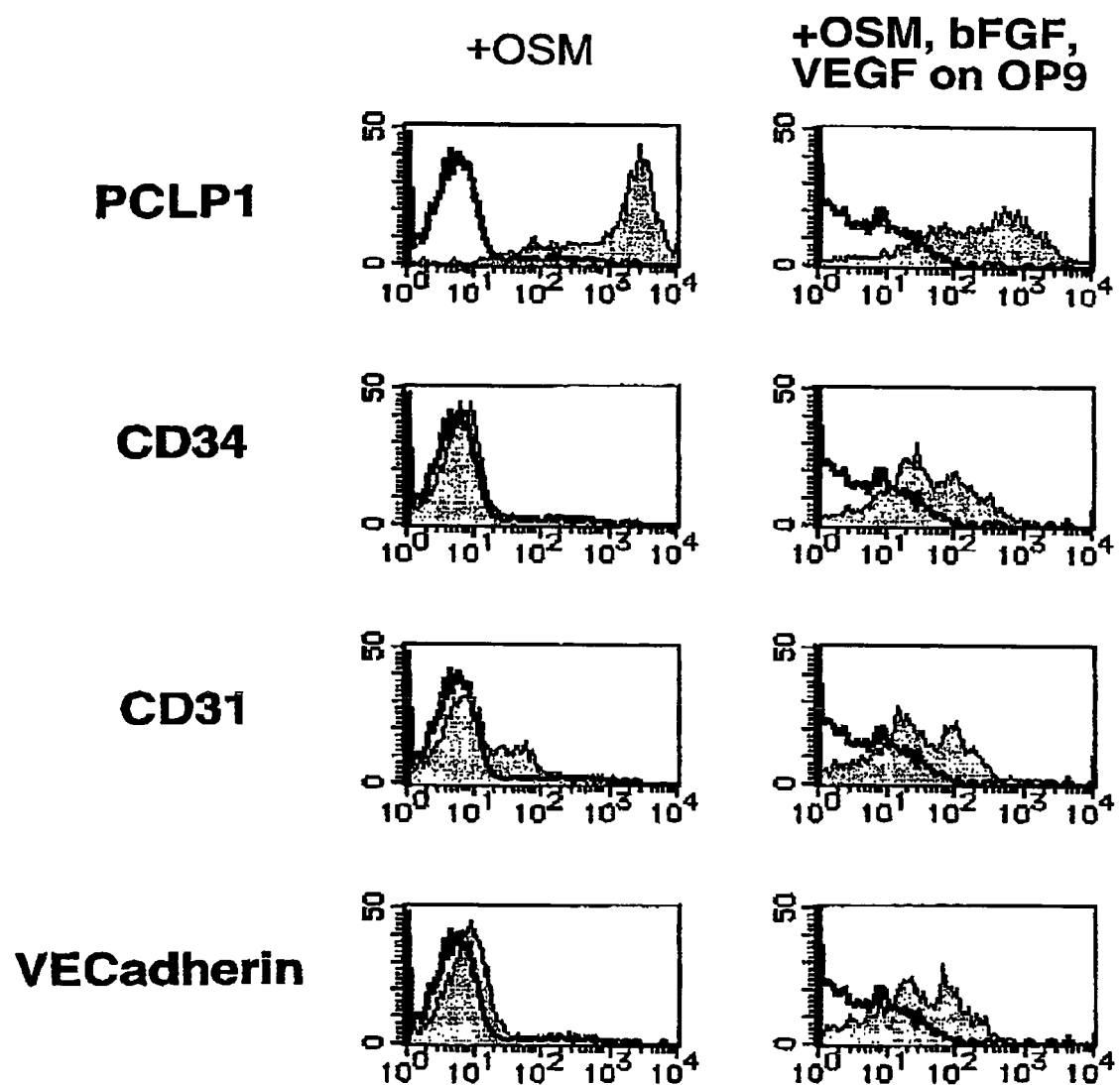

FIG. 15 is a diagram representing differentiation of PCLP1⁺CD45⁻ cells into endothelial cells.

Induction of the expression of various endothelial cell markers in PCLP1⁺CD45⁻ cells after co-culture with OP9 stromal cells for 10 days in the presence of OSM, VEGF, and bFGF. OP9 cells were gated out by the forward scatter window and the remaining major cell fraction was stained with antibodies as indicated. Left panels demonstrate FACS patterns of the PCLP1⁺CD45⁻ cells after 6 days in culture in the absence of OP9. Blank and light shaded peaks show staining patterns of isotype control and specific antibodies, respectively.

Figure 16:
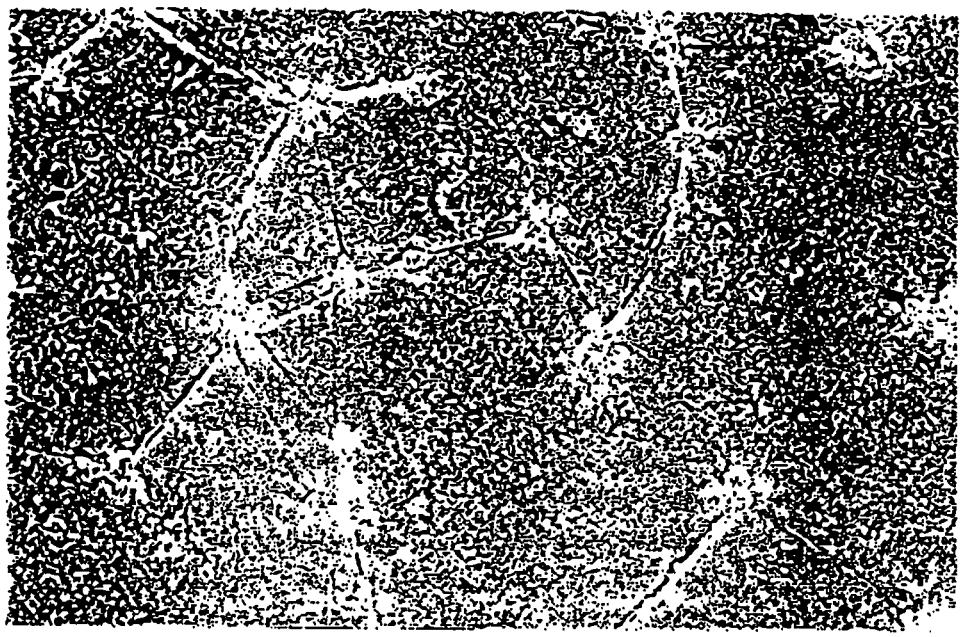

FIG. 16 is a photograph representing differentiation of PCLP1⁺CD45⁻ cells into endothelial cells.

Shows vascular network formation of the endothelial cells. After 10 days in co-culture of the PCLP1⁺CD45⁻ cells with OP9, cells were placed on the matrigel and cultured for 12 hours.

Figure 17:
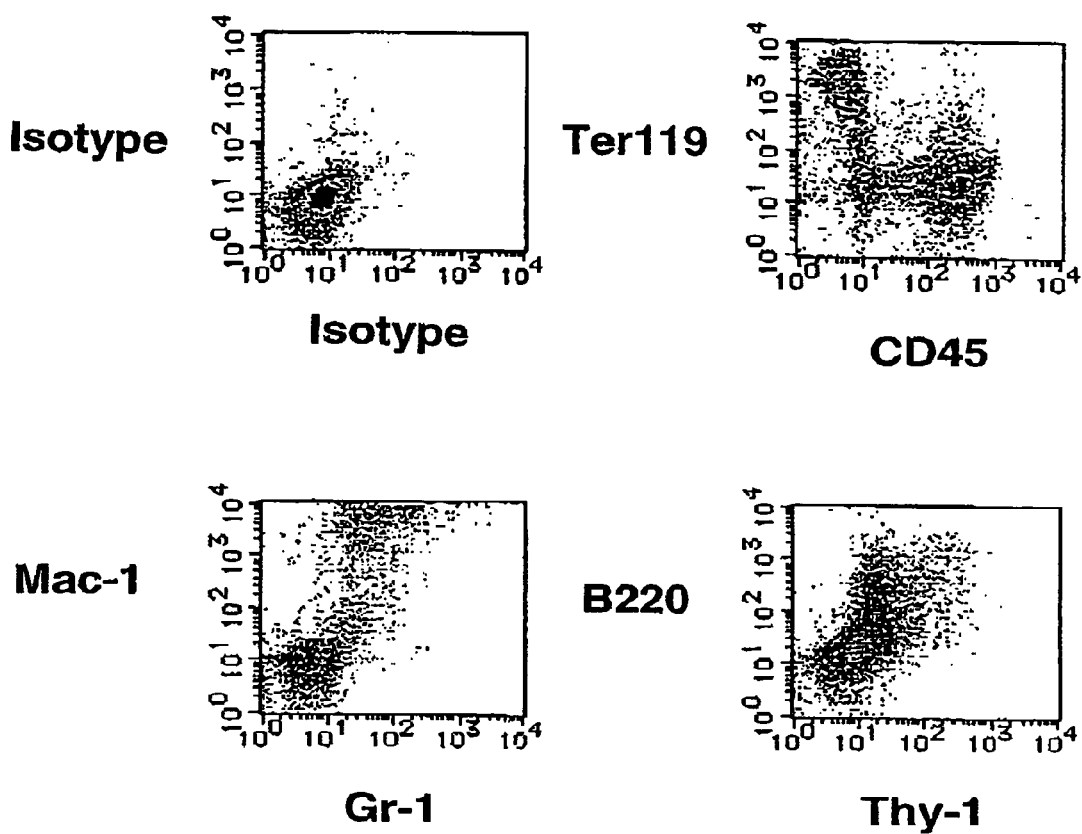

FIG. 17 is a diagram representing generation of hematopoietic cells from PCLP1⁺CD45⁻ cells in vitro.

The PCLP1⁺CD45⁻ cells isolated from the AGM region were co-cultured with OP9 stromal cells in the presence of SCF, bFGF, OSM, LIF, IL-3, and EPO for 10 days. Floating cells were double-stained with two anti-hematopoietic lineage marker antibodies or isotype controls as indicated and subjected to FACS analysis.

Figure 18:
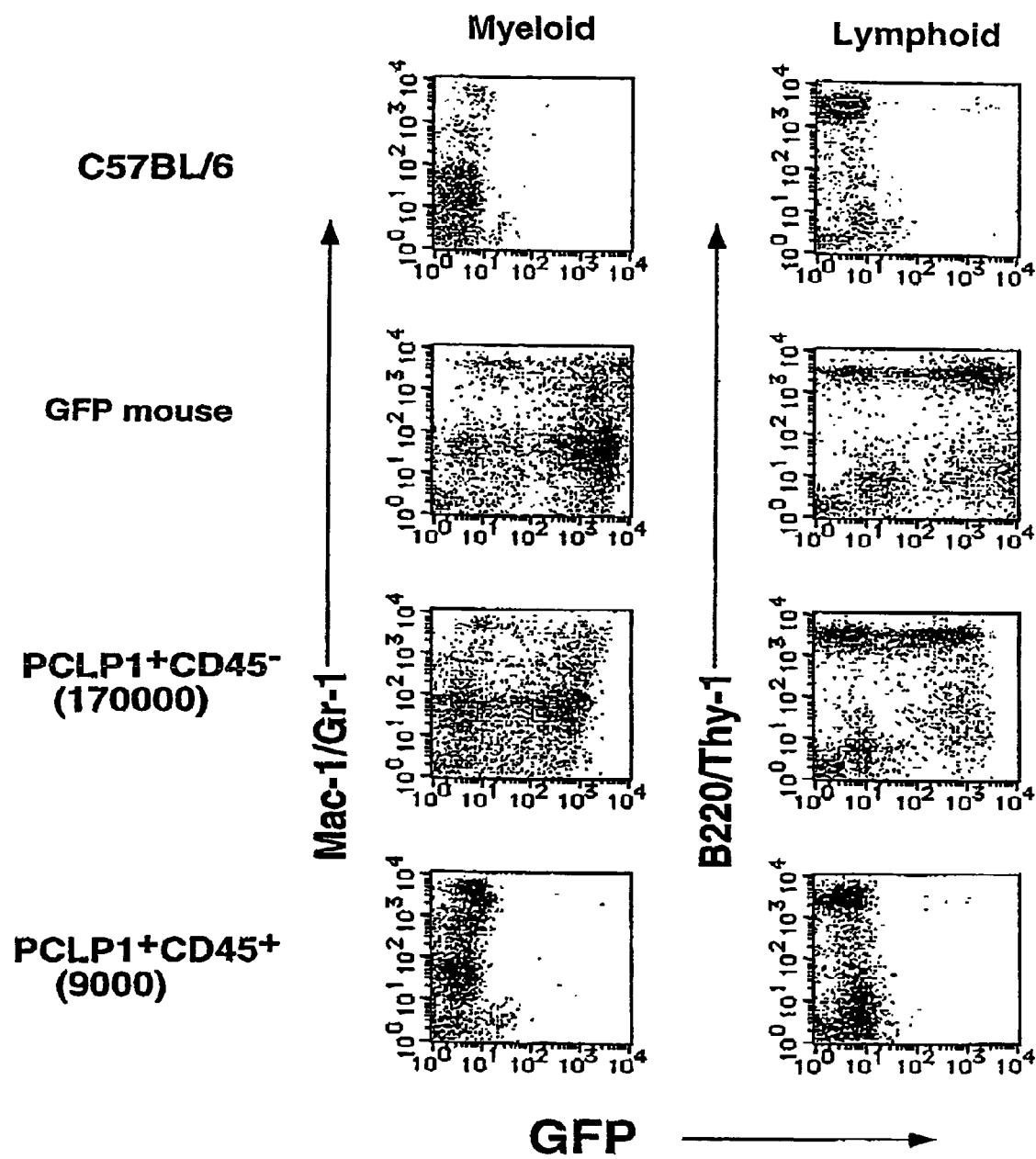

FIG. 18 is a diagram representing induction of long-term repopulating hematopoietic stem cells in vivo from PCLP1⁺CD45⁻ hemangioblasts.

GFP⁺PCLP1⁺CD45⁻ cells were isolated from the AGM region of the GFP transgenic mice and $1.7 \times 10^5$ cells were injected into the liver of neonatal C57BL/6 mice at 36 h after birth. After 6 months, peripheral blood was taken from one mouse (10B3 mouse) and mononuclear cells were stained with various antibodies against hematopoietic lineage markers as indicated. FACS patterns of C57BL/6 and GFP mouse are shown as negative and positive controls, respectively. Note the higher contribution of the donor-derived cells in the hematopoietic system of the 10B3 mouse.

Figure 19:
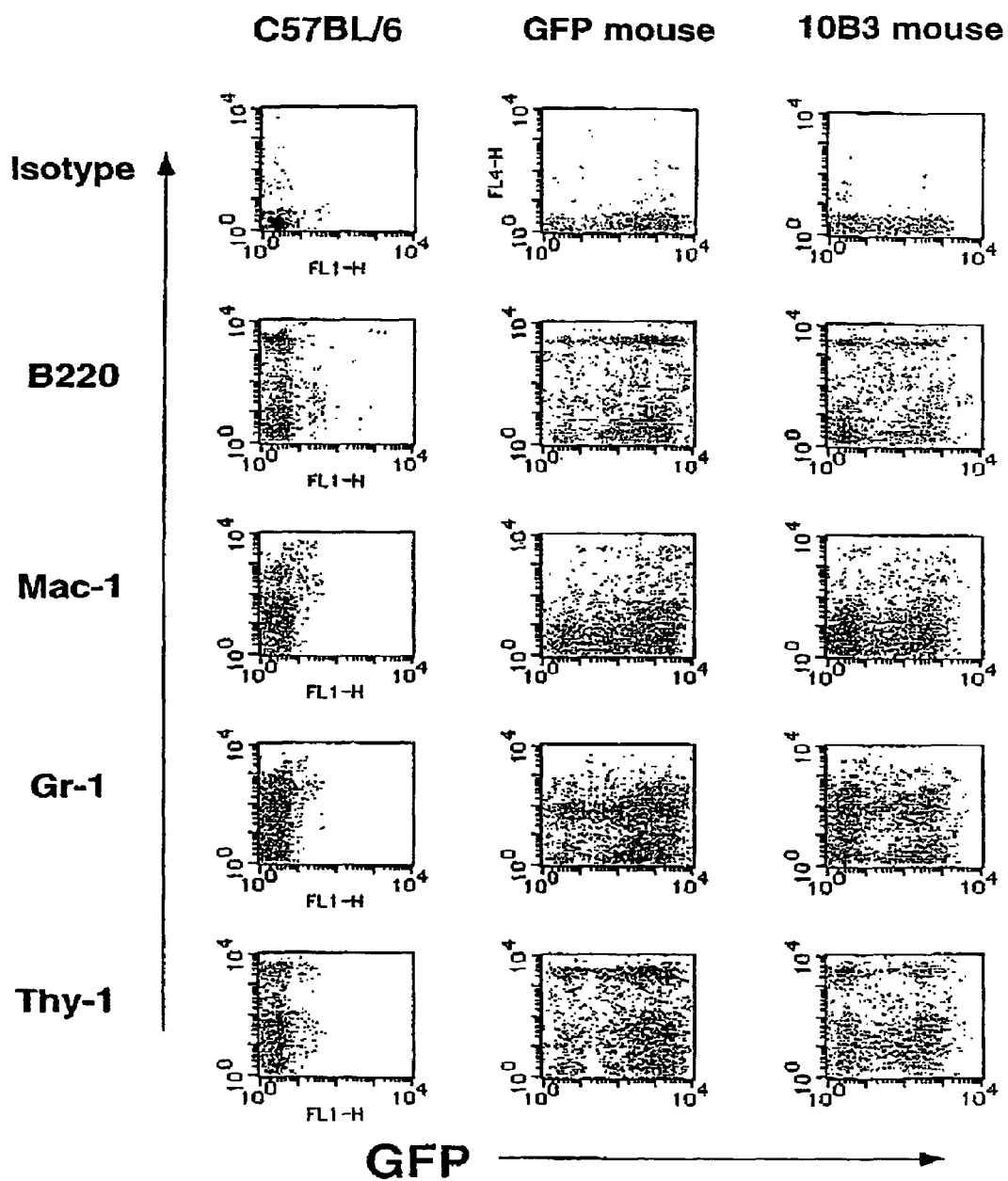

FIG. 19 is a diagram representing the induction of long-term repopulating hematopoietic stem cells from PLCP1⁺CD45⁻ hemangioblasts in vivo. Spleen was extracted from a similarly transplanted mouse as in FIG. 18, and mononuclear cells were stained with various antibodies against hematopoietic lineage markers as indicated.

Figure 20:
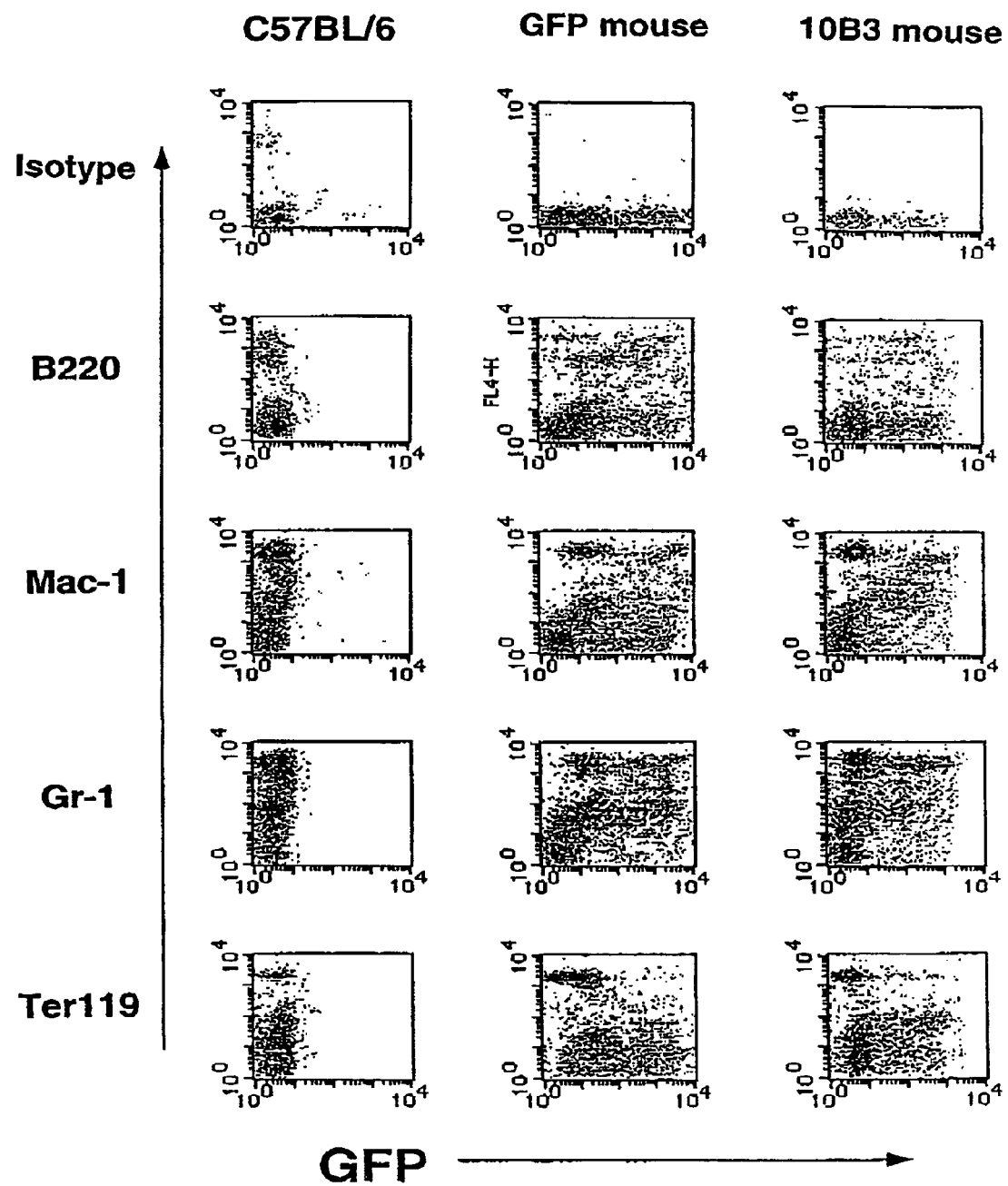

FIG. 20 is a diagram representing the induction of long-term repopulating hematopoietic stem cells from PLCP1⁺CD45⁻ hemangioblasts in vivo. Bone marrow was collected from a similarly transplanted mouse as in FIG. 18, and mononuclear cells were stained with various antibodies against hematopoietic lineage markers as indicated.

Figure 21:
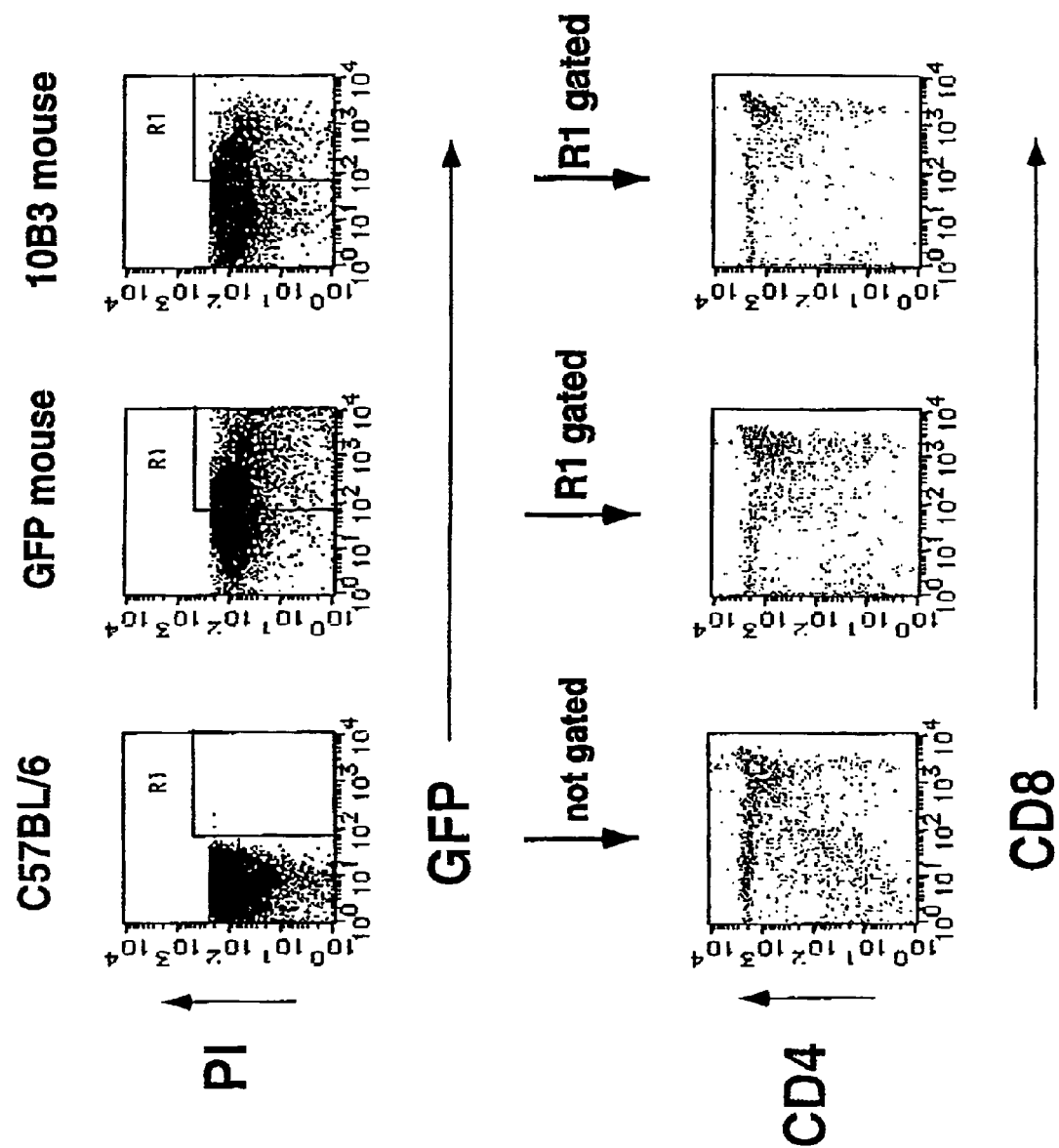

FIG. 21 is a diagram representing the induction of long-term repopulating hematopoietic stem cells from PLCP1⁺CD45⁻ hemangioblasts in vivo. Thymus was extracted from a similarly transplanted mouse as in FIG. 18, and mononuclear cells were stained with various antibodies against hematopoietic lineage markers as indicated. Analysis of thymus from 10B3 mouse was first performed gating GFP⁺ thymocytes to analyze the expression of CD4 and CD8.

BEST MODE FOR CARRYING OUT THE INVENTION

The present invention will be explained in detail below with reference to Examples, but it is not to be construed as being limited thereto.

Timed pregnant C57BL/6 mice were purchased from Nihon SLC (Hamamatsu, Japan). GFP transgenic mice (Okabe, M. et al. (1997) FEBS Lett. 407, 313-319) were maintained and mated in an animal facility. The time at midday (12:00) was taken to be 0.5 dpc for the plugged mice. As previously described (Mukouyama, Y. et al. (1998) Immunity 8, 105-114), AGM regions were dissected from mouse embryos at 11.5 dpc and a single cell suspension was subjected to primary culture.

Flow cytometry and cell sorting conducted in Examples are described below. Isolated AGM regions were dissociated by incubation with dispase (Boehringer) for 30 minutes at 37° C. and cell dissociation buffer (Gibco-BRL) for 30 minutes at 37° C., followed by vigorous agitation to separate cells. Single cell suspensions of the AGM culture were prepared by incubating with cell dissociation buffer for 30 minutes at 37° C.

Cells were first incubated with 50 μl of mouse serum on ice for 30 minutes and biotinylated primary antibody was added at 10 μg/ml. After a 30 minute incubation on ice, a 20-fold volume of phosphate buffered saline at pH 7.4 (PBS) containing FCS was added and the cells were centrifuged. Cells were then incubated with allophycocyanin (APC)-conjugated streptavidin (Molecular probe, Eugene, Oreg.) at 10 μg/ml for 30 minutes on ice with or without phycoerythrin (PE)-conjugated antibody. After washing with 5% FCS-PBS, cells were resuspended in 0.5 ml of PBS containing propidium iodide (PI) (Sigma, St. Louis, Mo.) and analyzed by FACS Calibur (Becton Dickinson). PI-positive dead cells were excluded. The monoclonal antibodies used for FACS were anti-CD45 (30F11.1), anti-Mac-1 (M1/70), anti-Gr-1 (RB6-8C5), anti-Thy-1.2 (30-H12), anti-B220 (RA3-6B2), anti-Ter-119 (TER-119), anti-CD4 (GK1.5), anti-CD8 (53-6.7), anti-CD34 (RAM34), anti-CD31 (MEC13.3), anti-Flk1 (Avas12α1), and rat isotype control (R35-95), which were all purchased from Pharmingen. Anti-VECadherin antibody (VECD1) (Matsuyoshi, N. et al. (1997) Proc. Assoc. Am. Physicians 109, 362-371) was kindly provided by S, Nishikawa (Kyoto University).

For cell sorting, AGM regions from GFP positive embryos at 11.5 dpc were trypsinized as described above and cells ($10^7$/ml) were incubated with biotinylated anti-PCLP1 antibody at 10 μg/ml in 5% FCS-PBS on ice for 30 minutes. After washing with 20-fold volumes of 5% FCS-PBS, cells were stained with PE-conjugated anti-CD45 antibody (10 μg/ml) and APC-conjugated streptavidin (10 μg/ml) on ice for 30 minutes and subjected to cell sorting using FACS Vantage. In a typical case of cell sorting in combination with anti-PCLP1 and anti-CD45 antibodies as described below, out of $1.1 \times 10^7$ cells obtained from 40 AGM regions, $8.5 \times 10^5$ of PCLP1⁺CD45⁻ cells, $1.0 \times 10^6$ of PCLP1⁻CD45⁻ cells, and $5.9 \times 10^4$ of PCLP1⁺CD45⁺ cells were obtained by cell sorting.

EXAMPLE 1

Generation of Hematopoietic Cells in the AGM Culture

Figure 1:
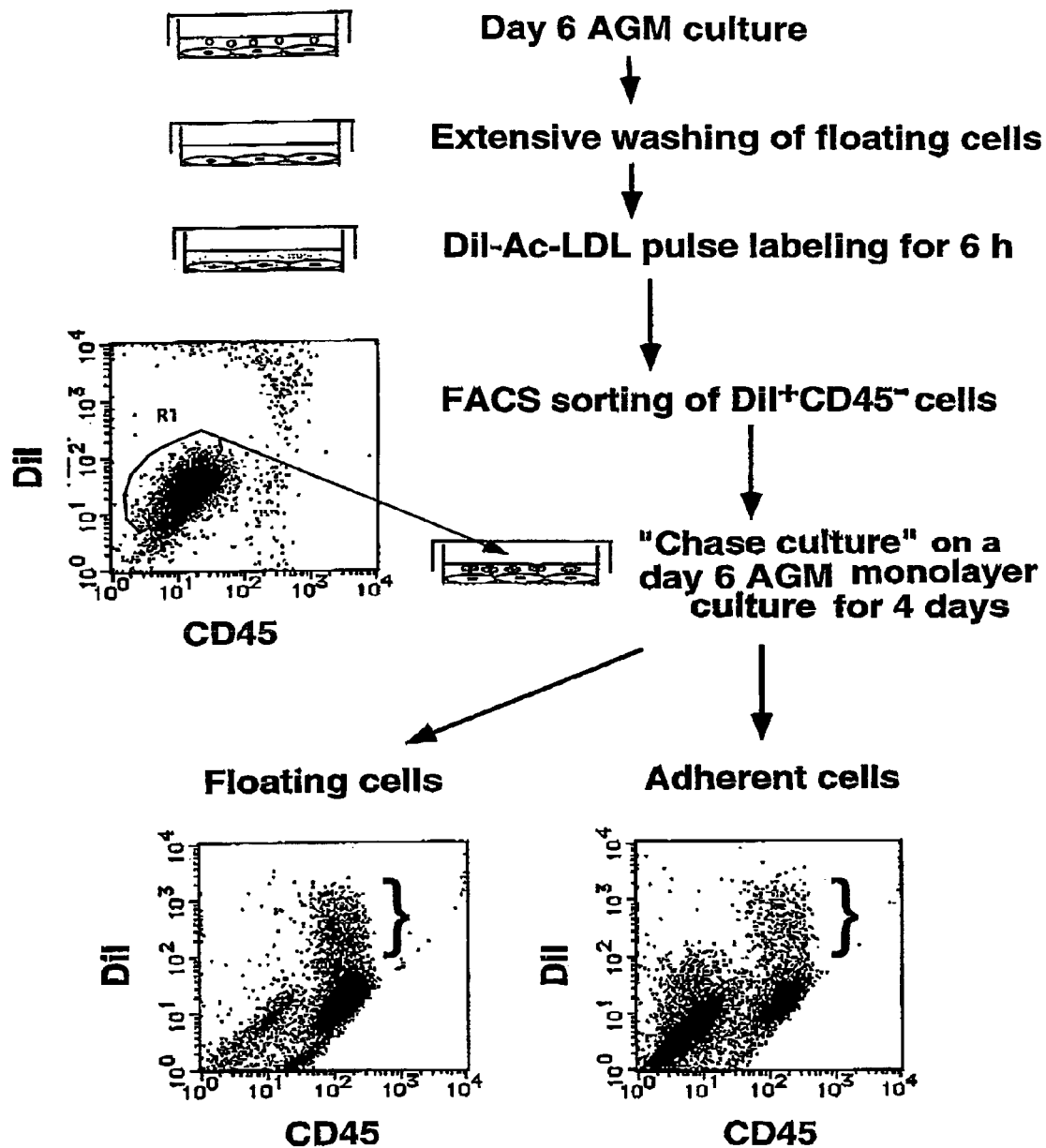
FIG. 1 is a diagram representing generation of hematopoietic cells from endothelial-like cells in an AGM culture.

The inventors' previous studies using an in vitro culture for AGM cells, they suggested that the endothelial-like cells in a AGM culture may contain hemangioblasts which give rise to hematopoietic progenitors in vitro (Mukouyama, Y. et al. (1998) Immunity 8, 105-114). Furthermore, timelap analysis of the cultured AGM cells under a phase contrast microscope showed that floating round cells with a hematopoietic appearance were spontaneously generated from adherent endothelial-like cells in situ (data not shown). To test the possibility that the adherent endothelial-like cells produced hematopoietic cells, the inventors examined the uptake of DiI-Ac-LDL, which is known to be incorporated only into endothelial cells and macrophages (Goldstein, J. L. et al. (1979) Proc. Natl. Acad. Sci. USA 76, 333-337; Voyta, J. C. et al. (1984) J. Cell Biol. 99, 2034-2040). As shown in FIG. 1, the inventors first incubated AGM cells for 6 days to generate endothelial-like cells. AGM cells at day 6 were washed well with the culture medium to remove hematopoietic cells, and co-incubated with 10 µg/ml of 1,1'-dioctadecyl-3,3,3',3'-tetramethylindocarbocyanine perchlorate (Biomedical Technologies, Inc., Stoughton, Mass.)-labeled acetylated low density lipoprotein (DiI-Ac-LDL) at 37° C. for 6 hours. After washing twice with PBS, AGM cells were stained with anti-CD45 antibodies (Pharmingen, San Diego, Calif.) conjugated fluorescein isothiocyanate (FITC). DiI$^+$CD45$^-$ cell population was sorted by FACS Vantage (Becton Dickinson, Bedford, Mass.) and inoculated to unlabeled AGM culture at day 6. DiI$^+$CD45$^+$ hematopoietic cells appeared after 4 days of co-incubation (FIG. 1). These DiI$^+$CD45$^{30}$ hematopoietic cells were sorted and subjected to CFU-C assay.

CFU-C assay was conducted as follows: Cells ($10^4$) were inoculated into 0.8% methylcellulose medium containing 20% fetal calf serum, IL-3 (100 ng/ml), IL-6 (kind gift from Ajinomoto, Kawasaki) (100 ng/ml), SCF (kind gift from Kirin Brewery, Takasaki, Japan) (100 ng/ml), and EPO (kind gift from Kirin Brewery) (2 U/ml) and cultured for 14 days as previously described (Mukouyama, Y et al. (1998) Immunity 8, 105-114). These hematopoietic cells formed colonies in the CFU-C assay (data not shown), suggesting that some hematopoietic progenitor cells were derived from the DiI$^+$CD45$^-$ endothelial-like cells in the AGM primary culture.

EXAMPLE 2

Preparation of Monoclonal Antibodies Against Surface Antigens of Endothelial-Like Cells Derived from AGM Culture To define hemangioblasts more precisely, the inventors aimed to obtain a specific antibody directed against hemangioblasts. By repeating the passage of adherent cells of the AGM culture in the presence of OSM, the inventors were able to establish a novel OSM-dependent endothelial-like cell line, LO. LO cells exhibit characteristics very similar to those of endothelial-like cells in the AGM culture, such as endothelial-like morphology, incorporation of DiI-Ac-LDL, and production of hematopoietic cells. The inventors used the LO cells as immunogens to raise monoclonal antibodies against cell surface antigens on LO cells as follows:

Wistar rats (Nihon SLC) were immunized with $10^7$ of LO cells in the presence of Freund's complete adjuvant (WAKO, Osaka, Japan) according to the standard immunization procedure (Hockfield, S. et al. (1993) "Selected Methods for Antibody and Nucleic Acid Probes", Volume 1 (New York: Cold Spring Harbor Laboratory Press)). Lymph nodes were dissociated and fused with mouse myeloma P3X cells using polyethylene glycol as previously described (Ogorochi, T. et al. (1992) Blood 79, 895-903) and hybridoma supernatants were screened for the production of anti-LO specific antibodies by FACS. 10B9 monoclonal antibody was chosen based on the specific staining of endothelial-like cells in the AGM culture. 10B9 antibody was produced in nude mice and purified by using E-Z-Sep (Pharmacia Biotech, Uppsala, Sweden). The isotype of the 10B9 antibody was determined by using the rat IgG isotyping kit (Serotec, Oxford, UK). Biotinylated 10B9 antibody was prepared by using Enzotin (Enzo Diagnostics, Syosset, N.Y.) according to the manufacturer's instruction.

Flow cytometry revealed that the antibody designated 10B9 (rat IgG1) exhibited very clear staining of LO cells (FIG. 2A) but not of NIH3T3 cells (data not shown). This antibody also stained endothelial-like cells in the AGM culture as described below (see FIG. 5).

EXAMPLE 3

Molecular Cloning of Mouse PCLP1 Molecule as a Possible Hemangioblast Antigen Next, using a standard expression cloning strategy with COS7 cells and 10B9 monoclonal antibody, the inventors isolated a cDNA clone encoding the 10B9 antigen.

Expression cloning of a cDNA encoding the 10B9 antigen was carried out by using COS7 cells as previously described (Harada, N. et al. (1990) Proc. Natl. Acad. Sci. USA 87, 857-861) except that magnetic beads conjugated with anti-rat IgG antibody (Dynabeads M-450) (Dynal, Oslo, Norway) were employed instead of plate panning. Briefly, COS7 cells were fused with spheroplasts of the cDNA plasmid library of LO cells (Tanaka, M. et al. (1999) Blood 93, 804-815) and stained with 10B9 antibody followed by Dynabead selection. Plasmid DNA mixture was harvested from the beads, amplified in E. coli and re-transfected into COS7 cells. This procedure was repeated 4 to 5 times until a single band of cDNA insert was recovered. As a result, the inventors isolated a cDNA clone of 1.9 kilobases encoding the 10B9 antigen.

DNA sequencing revealed that the C-terminal amino acid sequence was highly homologous to those of human and rabbit podocalyxin-like protein 1 (PCLP1) (Kershaw, D. B. et al. (1997) J. Biol. Chem. 272, 15708-15714; Kershaw, D. B. et al. (1995) J. Biol. Chem. 270, 29439-29446), suggesting that it was a mouse counterpart of PCLP1 (FIG. 3). The avian PCLP1 homolog, thrombomucin, also shares the conserved regions (McNagny, K. M. et al. (1997) J. Cell Biol. 138, 1395-1407) (FIG. 3). To obtain the full length mouse PCLP1 cDNA, the inventors isolated 5' cDNA fragments of mouse PCLP1 through screening of the original cDNA library and rapid amplification of the cDNA ends (RACE) method. 5'-RACE was performed using the 5'-RACE kit (GIBCO-BRL). The DNA sequences of the cDNAs were determined by using a Dye terminator cycle sequencing kit (Perkin Elmer, Foster City, Calif.) and an automated DNA sequencer (Applied Biosystems, Foster City, Calif.). The cDNA nucleotide sequence of mouse PCLP1 and the amino acid sequence of protein encoded by the cDNA are set forth in SEQ ID NO: 1 and 2, respectively.

COS7 cells were transfected with the reconstructed full length mouse PCLP1 cDNA in the pME18S expression vector and were stained with 10B9 antibody. The COS7 cells transfected with PCLP1 cDNA exhibited specific staining with 10B9 antibody (FIG. 2B), confirming that the 10B9 antibody recognizes mouse PCLP1. PCLP1 is an extensively glycosylated protein with a single transmembrane region. As previously reported (Kershaw, D. B. et al. (1997) J. Biol. Chem. 272, 15708-15714; Kershaw, D. B. et al. (1995) J. Biol. Chem. 270, 29439-29446), the amino acid sequence of the N-terminal region of PCLP1 is poorly conserved among species (FIG. 3). Interestingly, a recent report suggested that both PCLP1 and CD34 are ligands for L-selectin in the high endothelial venule and that PCLP1 and CD34 share common amino acid sequences in their cytoplasmic tails (Sassetti, C. et al. (1998) J. Exp. Med. 187, 1965-1975). These homologous amino acid residues are also found in mouse PCLP1 at positions 440 to 451, 464 to 473 and 500 to 503 (FIG. 3).

For Northern blotting, poly(A)$^+$ RNA samples were electrophoretically separated in 1.0% agarose gel and transferred onto a nylon membrane (Boehringer Mannheim, Mannheim, Germany). The RNA was then hybridized with digoxigenin (DIG)-labeled single strand DNA probe for the PCLP1 cDNA (2.1 kb) as described previously (Tanaka, M. et al. (1999) Blood 93, 804-815)

PCLP1 was originally identified as a major component of podocytes in the rabbit kidney and demonstrated to be expressed in some endothelial cells (Kershaw, D. B. et al. (1995) J. Biol. Chem. 270, 29439-29446). Consistent with previous reports (Kershaw, D. B. et al. (1997) J. Biol. Chem. 272, 15708-15714; Kershaw, D. B. et al. (1995) J. Biol. Chem. 270, 29439-29446), the inventors detected PCLP1 mRNA in kidney, heart, lung, brain, and muscle, but not in spleen, thymus, small intestine, or liver of adult mice (FIG. 4). The same size of mRNA was also detected in LO cells (FIG. 4). The avian counterpart of PCLP-1, thrombomucin, was reported to be expressed in thrombocytes and multipotent hematopoietic progenitors (McNagny, K. M. et al. (1997) J. Cell Biol. 138, 1395-1407). Likewise, expression of PCLP1 was found in some bone marrow cells (data not shown) and hematopoietic cells in the AGM region (see FIG. 6, 8A) as described below.

EXAMPLE 4

Expression of PCLP1 on the Endothelial-Like Cells in the AGM Culture

The inventors examined the expression of PCLP1 on the endothelial-like cells in the AGM culture by immunostaining with 10B9 anti-PCLP1 antibody. Cultured AGM-derived cells in plastic plates were fixed with 1% paraformaldehyde (PFA)-PBS at room temperature for 15 minutes and incubated with anti-PCLP1 10B9 antibody at 10 μg/ml at 4° C. over night. After incubation with peroxidase-conjugated anti-rat IgG (Amersham), signals were visualized by 3,3'-diaminobenzidine (DAB) as previously described (Hara, T. et al. (1998) Dev. Biol. 201, 144-153).

Figure 8A:
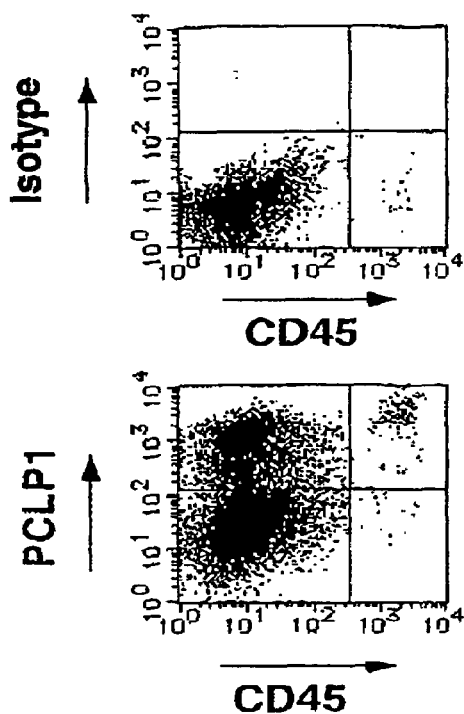
Figure 8B:
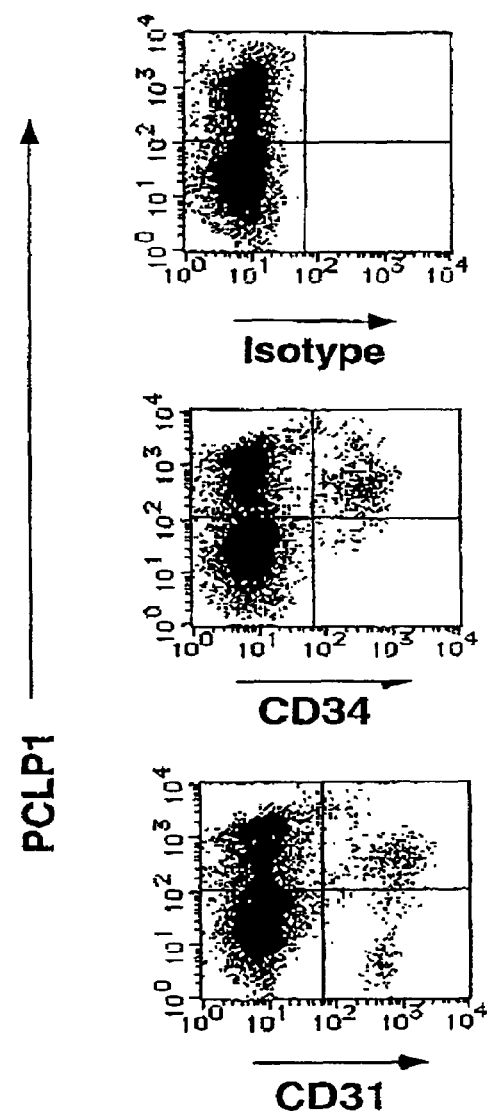

As the inventors expected, PCLP1 was detectable on endothelial-like cells (FIGS. 5A to C), but not on fibroblastic cells (data not shown) in the AGM culture. The endothelial-like cells, defined by their polygonal cell morphology and incorporation of DiI-Ac-LDL, were further fractionated by fluorescent activated cell sorting (FACS) using anti-PCLP1 and anti-CD45 antibodies (FIG. 6). Except for the erythroid lineage, CD45 is known to be a pan specific marker for hematopoietic cells including LTR-HSCs (Morrison, S. J. et al. (1995) Annu. Rev. Cell. Dev. Biol. 11, 35-71). It is noteworthy that hematopoietic cells (CD45$^+$) in the AGM culture also express a high level of PCLP1 (FIG. 6) as is the case for the AGM region (FIG. 8A).

To examine whether the PCLP1$^+$CD45$^-$ non-hematopoietic fraction contains hemangioblasts, PCLP1$^+$CD45$^-$ cells (2×10$^5$) were isolated (the R2 gate shown in FIG. 6) from the day 6 AGM culture of transgenic mice expressing green fluorescent protein (GFP) and were inoculated into the day 6 AGM culture of nontransgenic mice. After 4 days of incubation, GFP$^+$CD45$^+$ hematopoietic cells appeared in both floating and adherent fractions (FIG. 7), indicating that hematopoietic cells are generated from the PCLP1$^+$CD45$^-$ endothelial-like cells in the AGM primary culture. The adherent GFP$^+$CD45$^+$ cells may represent the hematopoietic cells present underneath the stromal cell layer.

EXAMPLE 5

Expression and Localization of PCLP1 in the AGM Region of a Mouse Embryo

The inventors next examined the presence of the PCLP1$^+$ CD45$^-$ cells in the intact AGM region of mouse embryos at 11.5 dpc. Based on FACS staining, there were more PCLP1$^+$ CD45$^-$ cells (32%) than PCLP1$^+$CD45$^+$ cells (1.5%) in the AGM region (FIG. 8A). The sorted PCLP1$^+$CD45$^-$ cells were adherent cells with the capacity to incorporate DiI-Ac-LDL (data not shown), indicating that these cells are endothelial-like cells. It was recently reported that hematogenic angioblasts in the yolk sac and the P-Sp region express Flk1, VECadherin, and CD34 (Nishikawa, S. I. et al. (1998) Immunity 8, 761-769). Thus, the inventors examined whether these molecules are expressed in the PCLP1$^+$CD45$^-$ fraction. Interestingly, a majority of nonhematopoietic CD34$^+$ cells, CD31$^+$ cells, and Flk1$^+$ cells also expressed PCLP1 (FIGS. 8B, 9C), whereas 79% of VECadherin$^+$CD45$^-$ cells were found in the PCLP1$^-$ fraction (FIG. 9D). Consistent with the overlapping expression patterns of PCLP1 and CD34, expression of these two proteins was localized in the endothelium of the dorsal aorta (FIGS. 10E, 10H) and in the genital ridge region (FIGS. 10F, 10I) of the mouse embryo at 11.5 dpc.

In situ hybridization analysis of the paraffin sections of a mouse embryo was conducted as follows. For preparation of paraffin sections, the caudal half of mouse embryos at 11.5 dpc was fixed in 4% PFA-PBS for 10 hours. Paraffin sections (6 μm thick) were prepared as previously described (Hara, T. et al. (1998) Dev. Biol. 201, 144-153) and placed on poly-L-lysine-coated slide glasses. After hydration of paraffin sections, the sections were stained with anti-PCLP1 or anti-CD34 antibody at 10 μg/ml at 4° C. over night and visualized as described above. Samples were counterstained with methylgreen.

In situ hybridization of the parrafin sections was carried out as previously described (Imakawa, K. et al. (1995) Endocrine 3, 511-517). DIG-labeled antisense and sense RNA probes were prepared by using the 5'-part of the PCLP1 cDNA fragment (nucleotide 126 to 354).

In situ hybridization analysis of the PCLP1 mRNA in the paraffin sections of a mouse embryo also revealed a similar expression pattern in the dorsal aorta (FIG. 11N) and the genital ridge (FIG. 11O). Since endothelial-like cells in the day 6 AGM culture do not express VECadherin and CD34 (data not shown), the inventors employed PCLP1 as a marker for the separation of hemangioblasts in the AGM region in the following Examples.

EXAMPLE 6

Endothelial Differentiation of the PCLP1⁺CD45⁻ Cells from the AGM Region

The PCLP1⁺CD45⁻ cell fraction was separated by cell sorting from the AGM region of mouse embryos at 11.5 dpc (the R1 gate in FIG. 12). The sorted cells were reanalyzed, but CD45⁺ cells were undetectable (FIG. 12). Even 3 hours after plating of the sorted PCLP1⁺CD45⁻ cells, no hematopoietic-like cells could be detected by microscopic observation and the cells were capable of incorporating DiI-Ac-LDL (data not shown). When these cells were cultured in the presence of OSM for 6 days, endothelial-like cells increased by 10-folds during incubation (FIG. 13), incorporated DiI-Ac-LDL and expressed Flk1 (FIG. 14 top and bottom), whereas no cells grew in the absence of OSM. Since only 12% of the sorted PCLP1⁺CD45⁻ cells were Flk1⁺ cells at the time of separation (FIG. 9C), Flk1⁺ cells may be selectively expanded or Flk1 expression may be induced during cultivation. The PCLP1⁺CD45⁻ cells grown in the presence of OSM were partially positive for CD31, negative for CD34, and very weakly positive for VECadherin (FIG. 15).

To test the possibility that the PCLP1⁺CD45⁻ cells differentiate to endothelial cells, the inventors employed the OP9 co-culture system that has been used to induce endothelial differentiation in vitro (Hamaguchi, I. et al. (1999) Blood 93, 1549-1556; Hirashima, M. et al. (1999) Blood 93, 1253-1263).

Mouse calvaria-derived OP9 cells (kindly provided by S, Nishikawa, Kyoto University) were passaged as previously described (Kodama, H. et al. (1994) Exp. Hematol. 22, 979-984). Sorted PCLP1⁺CD45⁻ cells from the AGM region were inoculated on subconfluent OP9 cells in a AGM culture medium containing various cytokines and cultured for 10 days. For the generation of hematopoietic cells, $5 \times 10^4$ cells were co-cultured with OP9 in the presence of SCF (100 ng/ml), bFGF (1 ng/ml), LIF (10 ng/ml), OSM (10 ng/ml), IL-3 (10 ng/ml), and EPO (2 U/ml). For endothelial cell differentiation, $10^4$ cells were co-cultured in the presence of OSM (10 ng/ml), bFGF (1 ng/ml), and VEGF (PeproTech, London, UK) (10 ng/ml).

For matrigel assays, cells ($2 \times 10^5$) were resuspended in Dulbecco's modified Eagle's medium containing 1% fetal calf serum and VEGF (10 ng/ml) and overlayed on a Biocoat matrigel basement membrane (Becton Dickinson) in a 6-well plate. After 12 hours in culture, network formation was microscopically observed.

The PCLP1⁺CD45⁻ cells from the AGM region were co-cultured with OP9 stromal cells for 10 days in the presence of OSM, VEGF, and bFGF as described above. The resultant cells expressed higher levels of CD34 and VECadherin (FIG. 15) than those in the initial cell population (FIG. 8B, 9D) or those cultured with OSM alone. Co-culture of the PCLP1⁺CD45⁻ cells with OP9 also resulted in an increased expression of CD31 and a decreased expression of PCLP1 (FIG. 15). Moreover, the OP9 co-cultured cells formed a vascular network on a matrigel plate (FIG. 16), while the cells grown without OP9 failed to form a network (data not shown). These results indicate that PCLP1⁺CD45⁻ cells in the AGM region are able to differentiate to endothelial cells in the presence of OP9, OSM, VEGF, and bFGF. Therefore, PCLP1⁺CD45⁻ cells are likely to be the endothelial precursor cells, i.e. angioblasts. Growth of the angioblasts in the AGM region appears to be OSM-dependent and their differentiation requires additional factors including VEGF, bFGF, and unknown factors produced from OP9 cells.

On the other hand, co-culture of PCLP1⁺CD45⁻ cells with OP9 cells in the presence of hematopoietic growth factors containing SCF, interleukin (IL)-3, and erythropoietin (EPO) resulted in the development of hematopoietic cells. The hematopoietic cells included Mac-1/Gr-1 positive myeloid cells, B220/Thy-1-positive lymphoid cells, and Ter119-positive erythroid cells (FIG. 17), suggesting that multiple lineages of hematopoietic cells were generated from the PCLP1⁺CD45⁻ cells in vitro. Generation of these hematopoietic cells was also OSM-dependent. Taken together with the data from the DiI-Ac-LDL labeling experiment (FIG. 1), it can be concluded that PCLP1⁺CD45⁻ cells in the AGM region contain hemangioblasts and angioblasts.

EXAMPLE 7

Generation of LTR-HSCs from the PCLP1⁺CD45⁻ Cells in the AGM Region

A major goal of this Example was to know whether hemangioblasts in the AGM region could give rise to LTR-HSCs in vivo. LTR-HSCs were detected among the hematopoietic progenitors expanded in the AGM culture by the standard repopulation assay using irradiated adult mice. However, it was revealed that they are more efficiently engrafted when injected into livers of busulfan-treated neonatal mice (data not shown). This is reasonable as LTR-HSCs generated in the AGM region seed the fetal liver in vivo before homing into the bone marrow. The inventors thus considered the possibility that if LTR-HSCs were generated from the hemangioblasts present in the AGM region, they would engraft the neonatal liver more efficiently than in irradiated adult mice, and verified that. According to a recently established procedure (Yoder, M. C. et al. (1996) Biol. Blood Marrow Transplant. 2, 59-67), the inventors injected the PCLP1⁺CD45⁻ cells from the AGM regions of GFP transgenic mouse embryos at 11.5 dpc into the busulfan-treated nontransgenic neonatal mice.

Transplantation of cells into busulfan-treated neonatal mice was performed as previously described (Yoder, M. C. et al. (1997) Immunity 7, 335-344) with a slight modification. Briefly, busulfan (Sigma) was intraperitoneally injected into pregnant C57BL/6 mice at 12.5 μg/g on pregnant day 17 and 18. Within 24 to 48 hours after birth, cells derived from GFP mice in 25 μl of PBS were injected into the liver of neonatal mice. Peripheral blood of recipient mice was taken at 2 or 6 months after transplantation and analyzed for GFP chimerism.

As summarized in Table 1, donor-derived GFP positive hematopoietic cells were detected in the peripheral blood of 7 out of 9 mice at 2 to 6 months after the injection of the GFP⁺PCLP1⁺CD45⁻ cells. To repopulate the donor-derived blood cells, an injection of $1.7 \times 10^5$ cells or more was required, indicating that a small fraction of the PCLP1⁺CD45⁻ cell population are capable of generating LTR-HSCs. In contrast, no donor-derived hematopoietic cells were found by injecting the same number of PCLP1⁻CD45⁻ cells from the AGM region (the R2 gate in FIG. 12) (Table 1). Moreover, injection of the PCLP1⁺CD45⁺ cells (0.9 to $2.1 \times 10^4$) did not contribute to GFP chimerism, which effectively excluded the possibility that a small number of contaminating CD45⁺ cells in the PCLP1⁺CD45⁻ fraction repopulated in the recipient mice. The chimerism was maintained up to 6 months in both myeloid and lymphoid compartments of the peripheral blood of a mouse (10B3 mouse) injected with 1.7×10⁵ of the PCLP1⁺CD45⁻ cells (FIG. 18). In the 10B3 mouse, all lineages of donor-derived GFP positive hematopoietic cells were repopulated in the spleen (FIG. 19) and bone marrow (FIG. 20). CD4/CD8-double positive and mature single positive T cells derived from the donor were also detected in the recipient thymus (FIG. 21). These results indicate that hemangioblasts with potential to generate LTR-HSCs are present in the PCLP1⁺CD45⁻ cell population of the AGM region. Although a similar number of the PCLP1⁺CD45⁻ cells derived from the day 6 AGM primary culture showed a decreased repopulation potential (Table 1), they were capable of generating hematopoietic cells in vitro (FIG. 7). Hence, the in vitro culture of the AGM cells negatively affected the repopulation potential of the PCLP1⁺CD45⁻ cells.

TABLE 1

Hematopoietic cell generation from PCLP1⁺CD45⁻ cells in engrafted mice

| Exp. | Cell | Fraction | Cell number/ mouse | Engrafted/Total (% Chimerism) |
|---|---|---|---|---|
| 1 | AGM | PCLP1⁺CD45⁻ | 1.7 × 10⁵ | 1/1* (53%) |
|   |   | PCLP1⁺CD45⁺ | 9.0 × 10³ | 0/1* |
| 2 | AGM | PCLP1⁺CD45⁻ | 2.8 × 10⁵ | 2/2 (21%, 1.2%) |
|   |   | PCLP1⁻CD45⁻ | 2.8 × 10⁵ | 0/3 |
| 3 | AGM | PCLP1⁺CD45⁻ | 3.4 × 10⁵ | 1/1 (29%) |
|   |   | PCLP1⁻CD45⁻ | 3.4 × 10⁵ | 0/1 |
| 4 | AGM | PCLP1⁺CD45⁻ | 2.2 × 10⁵ | 3/5 (4.4%, 2.6%, 1.5%) |
|   |   | PCLP1⁺CD45⁺ | 2.1 × 10⁴ | 0/4 |
| 5 | AGM culture | PCLP1⁺CD45⁻ | 3.0 × 10⁵ | 2/5 (0.35%, 0.23%) |
|   |   | PCLP1⁺CD45⁺ | 2.9 × 10⁴ | 0/2 |
| 6 | AGM culture | PCLP1⁺CD45⁻ | 3.0 × 10⁵ | 2/5 (0.14%, 0.14%) |
|   |   | PCLP1⁻CD45⁻ | 3.0 × 10⁵ | 0/2 |

[Each cell fraction was sorted from AGM region or AGM culture of GFP mice and injected into busulfan-treated neonatal mice. Peripheral blood was taken at 2 months (6 months for those marked "*") after injection and subjected to FACS analysis. Relative frequency of GFP⁺ cells in engrafted mice was calculated and expressed as "% chimerism".]

INDUSTRIAL APPLICABILITY

The present invention provides a method for preparing a cell fraction containing hemangioblasts capable of generating both endothelial cells and hematopoietic cells, and a marker molecule "PCLP1" for hemangioblasts utilized in the preparation. A cell fraction according to the present invention is capable of not only differentiating into endothelial-like cells and hematopoietic cells, but also of expressing a long-term hematopoietic function in vivo. The method of this invention enables the screening and separation of hemangioblasts in various tissues and cells. A cell fraction of this invention is not only useful, for example, in screening factors and drugs that regulate the proliferation and differentiation of hematopoietic stem cells, but could also be used for isolating novel cell markers for hemangioblasts and hematopoietic stem cells, or for screening antibodies used in cell sorting.

The invention claimed is:

1. A method for preparing a cell population containing hemangioblasts, comprising:
   (a) obtaining cells from the aorta-gonad-mesonephros (AGM) region;
   (b) detecting cells comprising a PCLP-1-positive phenotype;
   (c) isolating the cells comprising a PCLP1-positive phenotype from other cells;
   (d) identifying the isolated PCLP-1-positive cells having a CD45-negative phenotype; and
   (e) isolating cells which are PCLP-1-positive and CD45-negative,
thereby preparing a cell population containing hemangioblasts.

2. The method according to claim 1, wherein the cells comprising a PCLP-1 positive phenotype are detected using an anti-PCLP1 antibody.

3. The method according to claim 1, wherein the cell population generates or contains long-term repopulating hematopoietic stem cells (LTR-HSCs).

4. The method of claim 1, wherein the cells comprising a PCLP-1 positive phenotype are isolated using an anti-PCLP1 antibody.

* * * * *

SEQUENCE LISTING

<160> NUMBER OF SEQ ID NOS: 5

<210> SEQ ID NO 1
<211> LENGTH: 2131
<212> TYPE: DNA
<213> ORGANISM: Mus musculus
<220> FEATURE:
<221> NAME/KEY: CDS
<222> LOCATION: (171)..(1679)

<400> SEQUENCE: 1

```
gtgtcccagc ccagctctgc ggtaggcagg aggagcggcc ggatcgcgac tccggagttc      60
gcggccgtcg ccaggcctcc cggagcggcg ccgacgctcc cgctgtccgg acgcgcgacc     120
ctgcgccagc gccgcagcca cctgctcgga gtcccgggc gagcacaacc atg cct         176
                                                     Met Pro
                                                       1 ccc act acg gcg ctc tcc gcg ctg ctg ctg ctg cta ctg tcg cct gca        224
Pro Thr Thr Ala Leu Ser Ala Leu Leu Leu Leu Leu Ser Pro Ala
        5                  10                  15 tct cac tcc cat aat gga aat gag act agc aca tct gct atc aaa tct        272
Ser His Ser His Asn Gly Asn Glu Thr Ser Thr Ser Ala Ile Lys Ser
    20                  25                  30 agc act gtc cag agc cac caa agt gcc aca aca tca aca gaa gtc aca        320
Ser Thr Val Gln Ser His Gln Ser Ala Thr Thr Ser Thr Glu Val Thr
35                  40                  45                  50 act ggt cac cca gtg gca tct aca ctt gct tca acc cag cca agc aac        368
```

```
                                            -continued

Thr Gly His Pro Val Ala Ser Thr Leu Ala Ser Thr Gln Pro Ser Asn
            55                  60                  65 cct aca cca ttc aca acc tca acc caa tct cca ttt atg ccg acc tcc       416
Pro Thr Pro Phe Thr Thr Ser Thr Gln Ser Pro Phe Met Pro Thr Ser
                70                  75                  80 acc cca aac ccc acg agc aat caa agc ggt ggc aat ctg act tcc agt       464
Thr Pro Asn Pro Thr Ser Asn Gln Ser Gly Gly Asn Leu Thr Ser Ser
            85                  90                  95 gtc tcc gag gtg gac aag act aaa aca agc tct ccc agt agc acg gcc       512
Val Ser Glu Val Asp Lys Thr Lys Thr Ser Ser Pro Ser Ser Thr Ala
        100                 105                 110 ttc acc agt agc agt gga caa aca gcc tcc tct gga ggc aag agc ggt       560
Phe Thr Ser Ser Ser Gly Gln Thr Ala Ser Ser Gly Gly Lys Ser Gly
115                 120                 125                 130 gac agt ttt acc aca gcc cca aca acc act ttg ggg cta atc aac gtc       608
Asp Ser Phe Thr Thr Ala Pro Thr Thr Thr Leu Gly Leu Ile Asn Val
            135                 140                 145 tct tct cag cct act gac ctt aat acc acc tca aag ctt ctt tct acc       656
Ser Ser Gln Pro Thr Asp Leu Asn Thr Thr Ser Lys Leu Leu Ser Thr
            150                 155                 160 ccc aca aca gac aac aca aca agc cct cag cag cct gtg gat tct tca       704
Pro Thr Thr Asp Asn Thr Thr Ser Pro Gln Gln Pro Val Asp Ser Ser
        165                 170                 175 ccg agc aca gcg agc cat cct gtg ggg cag cat acc cct gct gct gtt       752
Pro Ser Thr Ala Ser His Pro Val Gly Gln His Thr Pro Ala Ala Val
180                 185                 190 ccc agc agc tct ggc tcc acg ccc agc act gac aac tct aca ctg aca       800
Pro Ser Ser Ser Gly Ser Thr Pro Ser Thr Asp Asn Ser Thr Leu Thr
195                 200                 205                 210 tgg aag ccc act aca cac aaa cca ttg ggc acc tct gaa gcc act cag       848
Trp Lys Pro Thr Thr His Lys Pro Leu Gly Thr Ser Glu Ala Thr Gln
            215                 220                 225 ccc ctc acc agc cag aca cca ggc atc act aca ttg ccc gtc tcc aca       896
Pro Leu Thr Ser Gln Thr Pro Gly Ile Thr Thr Leu Pro Val Ser Thr
            230                 235                 240 ctg caa cag tct atg gcg tct aca gtg gga act acg act gaa gag ttc       944
Leu Gln Gln Ser Met Ala Ser Thr Val Gly Thr Thr Thr Glu Glu Phe
        245                 250                 255 aca cac ctc atc tct aat ggg act ccc gtg gcc cct cca ggc ccc agc       992
Thr His Leu Ile Ser Asn Gly Thr Pro Val Ala Pro Pro Gly Pro Ser
        260                 265                 270 aca ccc tct ccc atc tgg gcc ttt gga aat tac cag cta aac tgt gaa      1040
Thr Pro Ser Pro Ile Trp Ala Phe Gly Asn Tyr Gln Leu Asn Cys Glu
275                 280                 285                 290 cct ccc ata agg cca gat gag gaa ctc ctt att ctg aac ctc aca aga      1088
Pro Pro Ile Arg Pro Asp Glu Glu Leu Leu Ile Leu Asn Leu Thr Arg
            295                 300                 305 gcc agc ctt tgc gaa agg agc cct ctg gat gag aaa gag aaa ctc gtg      1136
Ala Ser Leu Cys Glu Arg Ser Pro Leu Asp Glu Lys Glu Lys Leu Val
            310                 315                 320 gaa ctg ctg tgt cac tca gtc aaa gcg tcc ttc aag cca gct gag gat      1184
Glu Leu Leu Cys His Ser Val Lys Ala Ser Phe Lys Pro Ala Glu Asp
        325                 330                 335 ttg tgc act cta cat gtg gcc cct att cta gat aac cag gcg gtg gca      1232
Leu Cys Thr Leu His Val Ala Pro Ile Leu Asp Asn Gln Ala Val Ala
        340                 345                 350 gtg aag aga atc att atc gag acg aag ctt tct cct aag gcc gtg tat      1280
Val Lys Arg Ile Ile Ile Glu Thr Lys Leu Ser Pro Lys Ala Val Tyr
355                 360                 365                 370
```

-continued

```
gag cta ctg aag gac aga tgg gat gac ctg aca gag gcc gga gtc agt    1328
Glu Leu Leu Lys Asp Arg Trp Asp Asp Leu Thr Glu Ala Gly Val Ser
            375                 380                 385 gac atg aag ctg ggg aag gaa ggg cct cca gag gtc aat gag gac cgc    1376
Asp Met Lys Leu Gly Lys Glu Gly Pro Pro Glu Val Asn Glu Asp Arg
        390                 395                 400 ttc agc ctg ccg ctc atc atc acc atc gtc tgc atg gca tcc ttc ctg    1424
Phe Ser Leu Pro Leu Ile Ile Thr Ile Val Cys Met Ala Ser Phe Leu
    405                 410                 415 ctc ctt gtt gct gcc ctc tac ggc tgc tgt cac cag cgg atc tcc cag    1472
Leu Leu Val Ala Ala Leu Tyr Gly Cys Cys His Gln Arg Ile Ser Gln
420                 425                 430 agg aag gac cag caa cgg ctc aca gag gag ctg cag aca gtg gag aat    1520
Arg Lys Asp Gln Gln Arg Leu Thr Glu Glu Leu Gln Thr Val Glu Asn
435                 440                 445                 450 ggt tac cat gac aac cca acc ttg gaa gtg atg gag act cct tct gag    1568
Gly Tyr His Asp Asn Pro Thr Leu Glu Val Met Glu Thr Pro Ser Glu
                455                 460                 465 atg cag gag aag aag gtg gtc aac ctt aat ggg gag ctg ggg gac agt    1616
Met Gln Glu Lys Lys Val Val Asn Leu Asn Gly Glu Leu Gly Asp Ser
            470                 475                 480 tgg atc gtc cct ctg gac aac ttg acc aag gat gac cta gat gag gag    1664
Trp Ile Val Pro Leu Asp Asn Leu Thr Lys Asp Asp Leu Asp Glu Glu
        485                 490                 495 gaa gac aca cac ctc tgatctgtct gctggccacc ccaactgcac tgcagagctc    1719
Glu Asp Thr His Leu
    500 cagaccaccc aaagtgccat ttggacaggg aggggaaat cttcccacct gaagacagaa    1779 agactgggga gggagaatgg actccgaagg ttgtctccct cctcacaatc cctacagggc    1839 cttaattttc cttttcaagt tcaacaaagt cacattctgt ctagttccct catgtaaaat    1899 aacctacttg tgcctgagcc cagagcagga aggcaggagg aagatggaga acgccatgcg    1959 agtctctgga gctcctccag gaacggcacc ctctcatctc ataactgagg ccttaagagg    2019 tcaggtgact tgcacggggc cacacagccc tttggtgaca aaggttgttt ccctcagtct    2079 ggtgcttaat tgcatccaga cacactactg tgttcatctg tgcccattcc cc            2131

<210> SEQ ID NO 2
<211> LENGTH: 503
<212> TYPE: PRT
<213> ORGANISM: Mus musculus

<400> SEQUENCE: 2

Met Pro Pro Thr Thr Ala Leu Ser Ala Leu Leu Leu Leu Leu Leu Ser
1               5                   10                  15

Pro Ala Ser His Ser His Asn Gly Asn Glu Thr Ser Thr Ser Ala Ile
            20                  25                  30

Lys Ser Ser Thr Val Gln Ser His Gln Ser Ala Thr Thr Ser Thr Glu
        35                  40                  45

Val Thr Thr Gly His Pro Val Ala Ser Thr Leu Ala Ser Thr Gln Pro
    50                  55                  60

Ser Asn Pro Thr Pro Phe Thr Thr Ser Thr Gln Ser Pro Phe Met Pro
65                  70                  75                  80

Thr Ser Thr Pro Asn Pro Thr Ser Asn Gln Ser Gly Gly Asn Leu Thr
            85                  90                  95

Ser Ser Val Ser Glu Val Asp Lys Thr Lys Thr Ser Ser Pro Ser Ser
        100                 105                 110
```

```
Thr Ala Phe Thr Ser Ser Ser Gly Gln Thr Ala Ser Ser Gly Gly Lys
        115                 120                 125

Ser Gly Asp Ser Phe Thr Thr Ala Pro Thr Thr Thr Leu Gly Leu Ile
130                 135                 140

Asn Val Ser Ser Gln Pro Thr Asp Leu Asn Thr Thr Ser Lys Leu Leu
145                 150                 155                 160

Ser Thr Pro Thr Thr Asp Asn Thr Thr Ser Pro Gln Gln Pro Val Asp
            165                 170                 175

Ser Ser Pro Ser Thr Ala Ser His Pro Val Gly Gln His Thr Pro Ala
            180                 185                 190

Ala Val Pro Ser Ser Ser Gly Ser Thr Pro Ser Thr Asp Asn Ser Thr
            195                 200                 205

Leu Thr Trp Lys Pro Thr Thr His Lys Pro Leu Gly Thr Ser Glu Ala
210                 215                 220

Thr Gln Pro Leu Thr Ser Gln Thr Pro Gly Ile Thr Thr Leu Pro Val
225                 230                 235                 240

Ser Thr Leu Gln Gln Ser Met Ala Ser Thr Val Gly Thr Thr Thr Glu
            245                 250                 255

Glu Phe Thr His Leu Ile Ser Asn Gly Thr Pro Val Ala Pro Pro Gly
            260                 265                 270

Pro Ser Thr Pro Ser Pro Ile Trp Ala Phe Gly Asn Tyr Gln Leu Asn
            275                 280                 285

Cys Glu Pro Pro Ile Arg Pro Asp Glu Glu Leu Leu Ile Leu Asn Leu
            290                 295                 300

Thr Arg Ala Ser Leu Cys Glu Arg Ser Pro Leu Asp Glu Lys Glu Lys
305                 310                 315                 320

Leu Val Glu Leu Leu Cys His Ser Val Lys Ala Ser Phe Lys Pro Ala
            325                 330                 335

Glu Asp Leu Cys Thr Leu His Val Ala Pro Ile Leu Asp Asn Gln Ala
            340                 345                 350

Val Ala Val Lys Arg Ile Ile Ile Glu Thr Lys Leu Ser Pro Lys Ala
            355                 360                 365

Val Tyr Glu Leu Leu Lys Asp Arg Trp Asp Asp Leu Thr Glu Ala Gly
            370                 375                 380

Val Ser Asp Met Lys Leu Gly Lys Glu Gly Pro Pro Glu Val Asn Glu
385                 390                 395                 400

Asp Arg Phe Ser Leu Pro Leu Ile Ile Thr Ile Val Cys Met Ala Ser
            405                 410                 415

Phe Leu Leu Leu Val Ala Ala Leu Tyr Gly Cys Cys His Gln Arg Ile
            420                 425                 430

Ser Gln Arg Lys Asp Gln Gln Arg Leu Thr Glu Glu Leu Gln Thr Val
            435                 440                 445

Glu Asn Gly Tyr His Asp Asn Pro Thr Leu Glu Val Met Glu Thr Pro
450                 455                 460

Ser Glu Met Gln Glu Lys Lys Val Val Asn Leu Asn Gly Glu Leu Gly
465                 470                 475                 480

Asp Ser Trp Ile Val Pro Leu Asp Asn Leu Thr Lys Asp Asp Leu Asp
            485                 490                 495

Glu Glu Glu Asp Thr His Leu
            500

<210> SEQ ID NO 3
<211> LENGTH: 528
<212> TYPE: PRT
```

<213> ORGANISM: Homo sapiens

<400> SEQUENCE: 3

```
Met Arg Cys Ala Leu Ala Leu Ser Ala Leu Leu Leu Leu Ser Thr
 1               5                  10                  15

Pro Pro Leu Leu Pro Ser Ser Pro Ser Pro Ser Pro Ser Pro
                20                  25                  30

Ser Gln Asn Ala Thr Gln Thr Thr Asp Ser Ser Asn Lys Thr Ala
                35                  40                  45

Pro Thr Pro Ala Ser Ser Val Thr Ile Met Ala Thr Asp Thr Ala Gln
 50                  55                  60

Gln Ser Thr Val Pro Thr Ser Lys Ala Asn Glu Ile Leu Ala Ser Val
 65                  70                  75                  80

Lys Ala Thr Thr Leu Gly Val Ser Ser Asp Ser Pro Gly Thr Thr Thr
                85                  90                  95

Leu Ala Gln Gln Val Ser Gly Pro Val Asn Thr Thr Val Ala Arg Gly
                100                 105                 110

Gly Gly Ser Gly Asn Pro Thr Thr Thr Ile Glu Ser Pro Lys Ser Thr
                115                 120                 125

Lys Ser Ala Asp Thr Thr Thr Val Ala Thr Ser Thr Ala Thr Ala Lys
                130                 135                 140

Pro Asn Thr Thr Ser Ser Gln Asn Gly Ala Glu Asp Thr Thr Asn Ser
145                 150                 155                 160

Gly Gly Lys Ser Ser His Ser Val Thr Thr Asp Leu Thr Ser Thr Lys
                165                 170                 175

Ala Glu His Leu Thr Thr Pro His Pro Thr Ser Pro Leu Ser Pro Arg
                180                 185                 190

Gln Pro Thr Leu Thr His Pro Val Ala Thr Pro Thr Ser Ser Gly His
                195                 200                 205

Asp His Leu Met Lys Ile Ser Ser Ser Ser Thr Val Ala Ile Pro
                210                 215                 220

Gly Tyr Thr Phe Thr Ser Pro Gly Met Thr Thr Thr Leu Pro Ser Ser
225                 230                 235                 240

Val Ile Ser Gln Arg Thr Gln Gln Thr Ser Ser Gln Met Pro Ala Ser
                245                 250                 255

Ser Thr Ala Pro Ser Ser Gln Glu Thr Val Gln Pro Thr Ser Pro Ala
                260                 265                 270

Thr Ala Leu Arg Thr Pro Thr Leu Pro Glu Thr Met Ser Ser Ser Pro
                275                 280                 285

Thr Ala Ala Ser Thr Thr His Arg Tyr Pro Lys Thr Pro Ser Pro Thr
290                 295                 300

Val Ala His Glu Ser Asn Trp Ala Lys Cys Glu Asp Leu Glu Thr Gln
305                 310                 315                 320

Thr Gln Ser Glu Lys Gln Leu Val Leu Asn Leu Thr Gly Asn Thr Leu
                325                 330                 335

Cys Ala Gly Gly Ala Ser Asp Glu Lys Leu Ile Ser Leu Ile Cys Arg
                340                 345                 350

Ala Val Lys Ala Thr Phe Asn Pro Ala Gln Asp Lys Cys Gly Ile Arg
                355                 360                 365

Leu Ala Ser Val Pro Gly Ser Gln Thr Val Val Lys Glu Ile Thr
                370                 375                 380

Ile His Thr Lys Leu Pro Ala Lys Asp Val Tyr Glu Arg Leu Lys Asp
385                 390                 395                 400
```

```
Lys Trp Asp Glu Leu Lys Glu Ala Gly Val Ser Asp Met Lys Leu Gly
                405                 410                 415

Asp Gln Gly Pro Pro Glu Ala Glu Asp Arg Phe Ser Met Pro Leu
            420                 425                 430

Ile Ile Thr Ile Val Cys Met Ala Ser Phe Leu Leu Val Ala Ala
            435                 440                 445

Leu Tyr Gly Cys Cys His Gln Arg Leu Ser Gln Arg Lys Asp Gln Gln
450                 455                 460

Arg Leu Thr Glu Glu Leu Gln Thr Val Glu Asn Gly Tyr His Asp Asn
465                 470                 475                 480

Pro Thr Leu Glu Val Met Glu Thr Ser Ser Glu Met Gln Glu Lys Lys
                485                 490                 495

Val Val Ser Leu Asn Gly Glu Leu Gly Asp Ser Trp Ile Val Pro Leu
                500                 505                 510

Asp Asn Leu Thr Lys Asp Asp Leu Asp Glu Glu Glu Asp Thr His Leu
                515                 520                 525

<210> SEQ ID NO 4
<211> LENGTH: 551
<212> TYPE: PRT
<213> ORGANISM: Oryctolagus cuniculus

<400> SEQUENCE: 4

Met Arg Ser Ala Leu Ala Leu Ala Leu Leu Leu Leu Leu Leu Leu Ser
  1               5                  10                  15

Pro Pro Ser Leu Ser Gln Glu Lys Ser Pro Gln Pro Gly Pro Thr Pro
                20                  25                  30

Met Ala Thr Ser Thr Ser Thr Arg Pro Ala Pro Ala Ser Ala Pro Ala
            35                  40                  45

Pro Lys Ser Ser Val Ala Ala Ser Val Pro Ala Glu Gln Asn Thr Thr
    50                  55                  60

Pro Met Thr Thr Lys Ala Pro Ala Thr Gln Ser Pro Ser Ala Ser Pro
65                  70                  75                  80

Gly Ser Ser Val Glu Asn Ser Ala Pro Ala Gln Gly Ser Thr Thr Thr
                85                  90                  95

Gln Gln Ser Leu Ser Val Thr Thr Lys Ala Glu Ala Lys Asp Ala Gly
            100                 105                 110

Gly Val Pro Thr Ala His Val Thr Gly Ser Ala Arg Pro Val Thr Ser
        115                 120                 125

Gly Ser Gln Val Ala Ala Gln Asp Pro Ala Ala Ser Lys Ala Pro Ser
    130                 135                 140

Asn His Ser Ile Thr Thr Lys Pro Leu Ala Thr Glu Ala Thr Ser Gln
145                 150                 155                 160

Ala Pro Arg Gln Thr Thr Asp Val Gly Thr Pro Gly Pro Thr Ala Pro
                165                 170                 175

Pro Val Thr Asn Ser Thr Ser Pro Asp Leu Leu Gly His Ala Thr Pro
                180                 185                 190

Lys Pro Ser Glu Gly Pro Gln Leu Ser Phe Pro Thr Ala Ala Gly Ser
            195                 200                 205

Leu Gly Pro Val Thr Gly Ser Gly Thr Gly Ser Gly Thr Leu Ser Thr
        210                 215                 220

Pro Gln Gly Lys Pro Ala Thr Leu Thr Pro Val Ala Ser Ser Ala Glu
225                 230                 235                 240

Thr Gln Gly Met Pro Ser Pro Met Pro Pro Ser Pro Ala Ser Pro Ser
                245                 250                 255
```

```
Ser Ser Pro Phe Pro Ser Ser Pro Ser Pro Ala Leu Gln Pro
            260             265             270

Ser Gly Pro Ser Ala Ala Gly Thr Glu Asp Thr Thr Gly Arg Gly Pro
            275             280             285

Thr Ser Ser Ser Thr Glu Leu Ala Ser Thr Ala Leu His Gly Pro Ser
    290             295             300

Thr Leu Ser Pro Thr Ser Ala Val Arg Asp Gln Arg Val Ser Cys Gly
305             310             315             320

Pro Pro Glu Arg Pro Thr Glu Gln Leu Leu Ile Leu Asn Leu Thr Arg
                325             330             335

Ser Ser Pro Cys Ile His Val Phe Gln Arg Gln Ser Gln Gly Glu Gly
            340             345             350

Glu Thr Glu Ile Ser Met His Ser Thr Asp Ser Leu Pro Glu Asp Lys
            355             360             365

Leu Val Thr Leu Leu Cys Arg Ala Ala Lys Pro Thr Phe Asn Pro Ala
        370             375             380

Gln Asp Gln Cys His Val Leu Leu Ala Pro Met Leu Gly Ser His Ala
385             390             395             400

Val Val Val Lys Glu Ile Thr Ile Lys Thr Asn Leu Leu Pro Thr Ala
                405             410             415

Val Phe Glu Leu Leu Lys Asp Arg Trp Asp Leu Arg Glu Glu Gly
            420             425             430

Val Ser Asp Met Gln Leu Gly Asp Gln Gly Pro Pro Glu Glu Thr Glu
            435             440             445

Asp Arg Phe Ser Leu Pro Leu Ile Ile Thr Ile Val Cys Met Ala Ser
        450             455             460

Phe Leu Leu Leu Val Ala Ala Leu Tyr Gly Cys Cys His Gln Arg Leu
465             470             475             480

Ser His Arg Lys Asp Gln Gln Arg Leu Thr Glu Glu Leu Gln Thr Val
                485             490             495

Glu Asn Gly Tyr His Asp Asn Pro Thr Leu Glu Val Met Glu Thr Ser
            500             505             510

Ala Glu Met Gln Glu Lys Lys Val Val Asn Leu Asn Gly Glu Leu Gly
            515             520             525

Asp Ser Trp Ile Val Pro Leu Asp Asn Leu Thr Lys Asp Asp Leu Asp
            530             535             540

Glu Glu Glu Asp Thr His Leu
545                 550

<210> SEQ ID NO 5
<211> LENGTH: 571
<212> TYPE: PRT
<213> ORGANISM: Gallus gallus

<400> SEQUENCE: 5

Met Arg Ala Pro Leu Leu Leu Pro Leu Leu Pro Leu Leu Leu Phe Gly
  1               5                  10                  15

Val Ser Ser Gly Asn Asn Asp Lys Thr Thr His Ser Thr Thr Val Ser
            20                  25                  30

Pro Glu Thr Thr Lys Gln Ile Thr Thr Ile Thr Val Thr Thr Ser Gln
        35                  40                  45

Val Gln Gly Ser Ile Ser Ala Ser Lys Pro Ser Ser Thr Ala Pro Thr
    50                  55                  60

Ala Val Met Ser Phe Thr Lys Ala Gln Glu Ala Ala Thr Ser Ser Lys
```

```
            65                  70                  75                  80
Gln His Asp Ser Ser Thr Ser Ser Ile Pro Pro Ser Thr Ser Ile
                    85                  90                  95

Thr Pro Ser Ile Ile Thr Thr Ser Pro Gln Gly Lys Thr Pro Ser Thr
                100                 105                 110

Pro Ala Leu Thr His Thr Pro Asp Gln Asn Thr Lys Thr Thr Gly Arg
            115                 120                 125

Gln Asp Asp Thr Ser His Val Ser Val Ala Ser Thr Ser Ala Ser Gln
        130                 135                 140

Gln Val Ser Ser Ser Ala Ser Ala Ala Val Pro Thr Thr Thr Ser Ala
145                 150                 155                 160

Val Thr Ser Ser Ala Thr Gln Gln Lys Val Ser Pro Thr Asp Ser Ser
                165                 170                 175

Glu Ile Leu Leu Lys Pro Ser Ala Ser Pro Asn Ser Thr Gln Val Thr
                180                 185                 190

Ser Pro Ser Arg Thr Pro Lys Gly Phe Leu Ser Thr Val Thr Thr Ser
            195                 200                 205

Pro His Ile Ala Asp Asn Gly Ser Thr Ala Leu Asn Gln Leu Lys Ser
        210                 215                 220

Thr Val Ser Ser Glu Val Pro Val Ser Ser Phe Leu Asp Lys Asp
225                 230                 235                 240

His Ser Val Ser Ser Thr Ser Ala Thr Asn Gln His Leu Ser Leu
                245                 250                 255

Ser Ser His Arg Pro Thr Ser Pro Val Pro Lys Phe Glu Cys Ser Thr
            260                 265                 270

Pro His Ser Gly Ser Val Pro Ser Thr Ser Ser Lys Thr Ser Leu Ser
        275                 280                 285

Ser Pro Ser Ser Ser Thr Lys Asn Ala Thr Val Thr Thr Met Thr
290                 295                 300

Thr Ala Lys Ala Ala Tyr Thr Ser Gln Gly Asp Gly Ser Val Thr His
305                 310                 315                 320

Lys Ser Gly Val Thr Ala Gln Ser Pro Thr Ser Ala Pro Leu Pro Thr
                325                 330                 335

Pro Thr Leu Lys Asp His Met Lys Ser Lys Ser Pro Asp Gln Thr His
                340                 345                 350

Ser Asn Val Ser Pro Pro Asn Glu Val Ile Cys Glu Asp Gln Ile Gly
            355                 360                 365

Glu Val Arg Pro Ile Leu Asn Leu Lys Glu Lys Thr Cys Asp Asp
        370                 375                 380

Trp Lys Lys Ala Ser Asn Glu Ala Phe Phe Glu Val Phe Cys Ser Gly
385                 390                 395                 400

Arg Arg His Ala Phe Asn Ser Thr Arg Asp Arg Cys Thr Val Lys Leu
                405                 410                 415

Ala Ser Ser Asn His Arg Arg Trp Ala Val His Val Ile Val His Arg
                420                 425                 430

Val Leu Asp Pro Ala Ala Val Phe Glu Glu Leu Lys Glu Lys Arg Asn
            435                 440                 445

Glu Leu Glu Lys Leu Gly Ile Thr Asn Val Thr Tyr Leu Asn Gln Glu
        450                 455                 460

Met Glu Glu Glu Ile Lys Asp Gln Ser Ser Thr Pro Leu Ile Ile Thr
465                 470                 475                 480

Ile Val Thr Leu Ala Gly Ser Leu Leu Leu Ile Ala Ala Ile Tyr Gly
                485                 490                 495
```

-continued

```
Cys Cys His Gln Arg Phe Ser Gln Lys Lys Ser Gln Gln Arg Leu Thr
        500             505             510
Glu Glu Leu Gln Thr Met Glu Asn Gly Tyr His Asp Asn Pro Thr Leu
        515             520             525
Glu Val Met Glu Thr Gly Ser Glu Met Gln Glu Lys Lys Val Asn Leu
        530             535             540
Asn Gly Glu Leu Gly Asp Ser Trp Ile Val Pro Leu Asp Thr Ile Met
545             550             555             560
Lys Glu Asp Leu Glu Glu Glu Asp Thr His Leu
            565             570
```